US006572906B1

United States Patent
Higashimura et al.

(10) Patent No.: US 6,572,906 B1
(45) Date of Patent: Jun. 3, 2003

(54) METHOD FOR INHIBITING FADING OF A NATURAL PIGMENT USING NIGEROOLIGOSACCHARIDE OR MALTOOLIGOSACCHARIDE OR PANOSE WITH OR WITHOUT AN ANTIOXIDANT

(75) Inventors: Yutaka Higashimura, Toyonaka (JP); Kazuhiro Emura, Toyonaka (JP); Noriko Kuze, Toyonaka (JP); Junko Shirai, Toyonaka (JP); Takatoshi Koda, Toyonaka (JP)

(73) Assignee: San-Ei Gen F.F.I., Inc., Osaka-fu (JP)

( * ) Notice: Subject to any disclaimer, the term of this patent is extended or adjusted under 35 U.S.C. 154(b) by 69 days.

(21) Appl. No.: 09/594,736

(22) Filed: Jun. 16, 2000

(30) Foreign Application Priority Data

Mar. 16, 2000 (JP) .......................................... 2000-074306

(51) Int. Cl.[7] .............................. A23L 1/27; A23L 1/272
(52) U.S. Cl. ........................ 426/262; 426/268; 426/540; 426/541
(58) Field of Search ................................ 426/262, 268, 426/540, 541; 430/216

(56) References Cited

U.S. PATENT DOCUMENTS

| 4,751,091 A | * | 6/1988 | Nip et al. ..................... 426/268 |
| 4,859,564 A | * | 8/1989 | Tomiyama .................... 430/216 |
| 6,056,980 A | | 5/2000 | Unno et al. .................... 426/48 |

FOREIGN PATENT DOCUMENTS

| JP | 51-36223 A | 3/1976 |
| JP | 10-117747 A | 5/1998 |

* cited by examiner

Primary Examiner—Helen Pratt
(74) Attorney, Agent, or Firm—Sughrue Mion, PLLC

(57) ABSTRACT

The present invention provide an anti-fading agent for a pigment, characterized by comprising as active ingredients at least one oligosaccharide selected from the group consisting of nigerooligosaccharide, maltooligosaccharide and panose, when so required, in addition of an antioxidant. The anti-fading agent of the invention can advantageously inhibit fading in colors (including fading in colors by light irradiation and heat treatment) of natural pigments such as anthocyanin-based pigments, flavonoid-based pigments, carotenoid-based pigments and the like, and is useful for colored beverage and food products, pharmaceutical drugs, cosmetics and the like with which the fading in colors may be a problem.

7 Claims, 21 Drawing Sheets

LIGHT RESISTANCE OF RED CABBAGE PIGMENT

FIG. 11
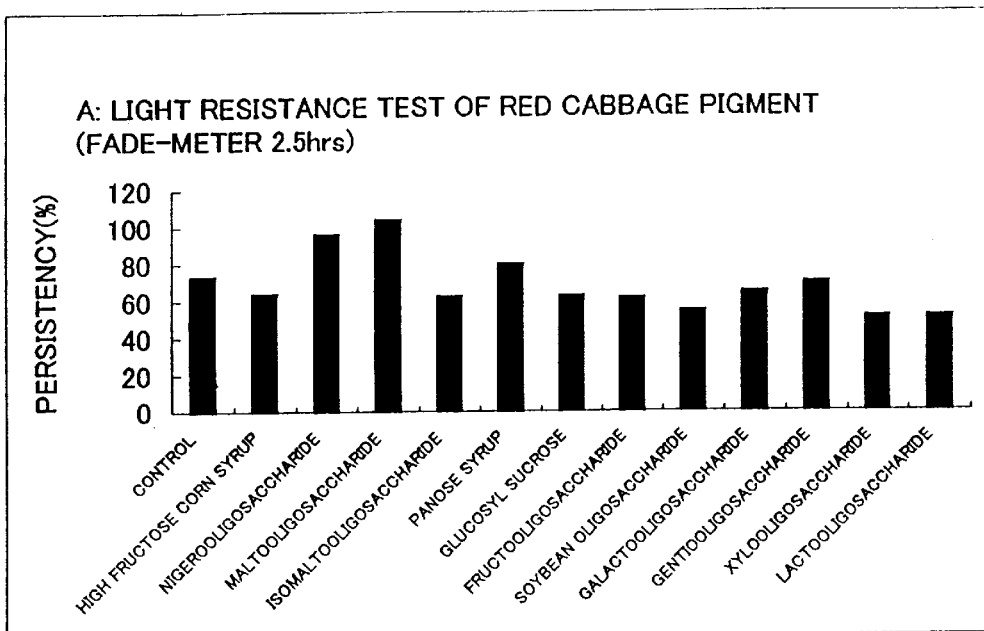
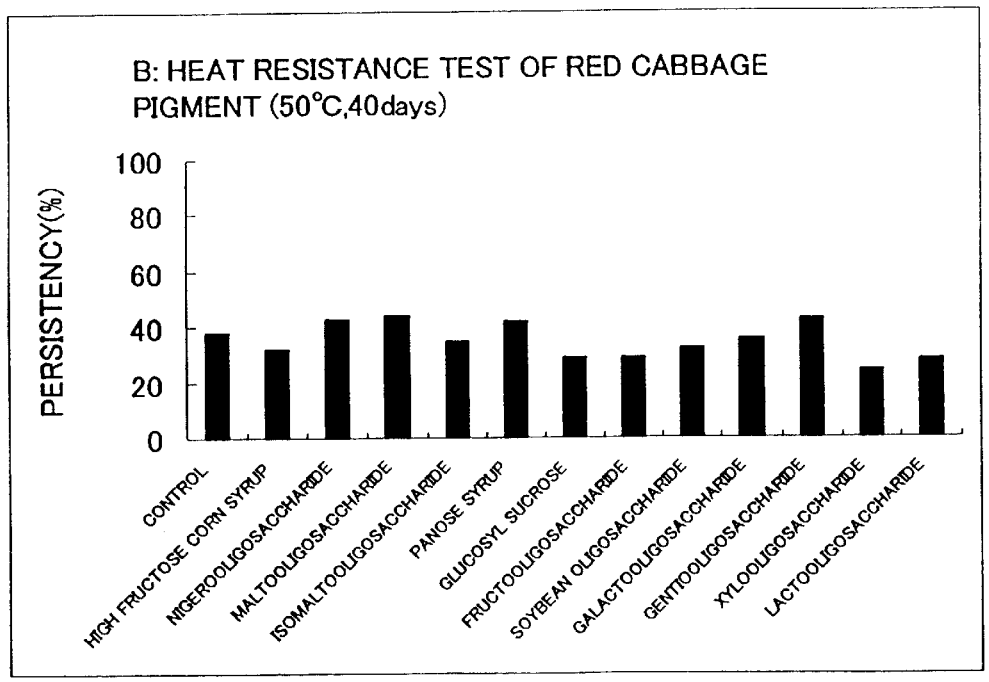

FIG. 12
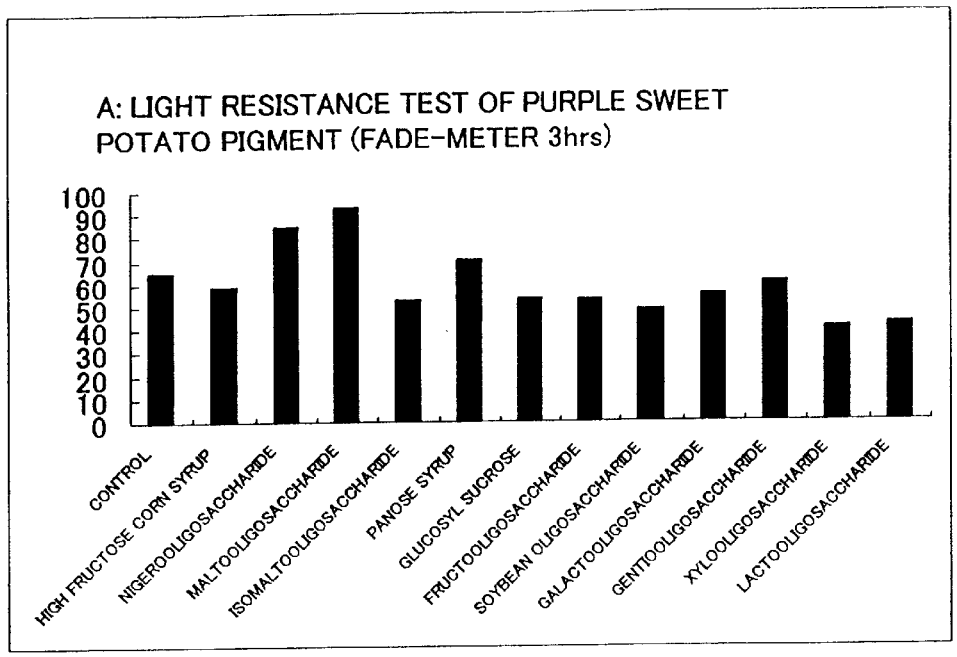
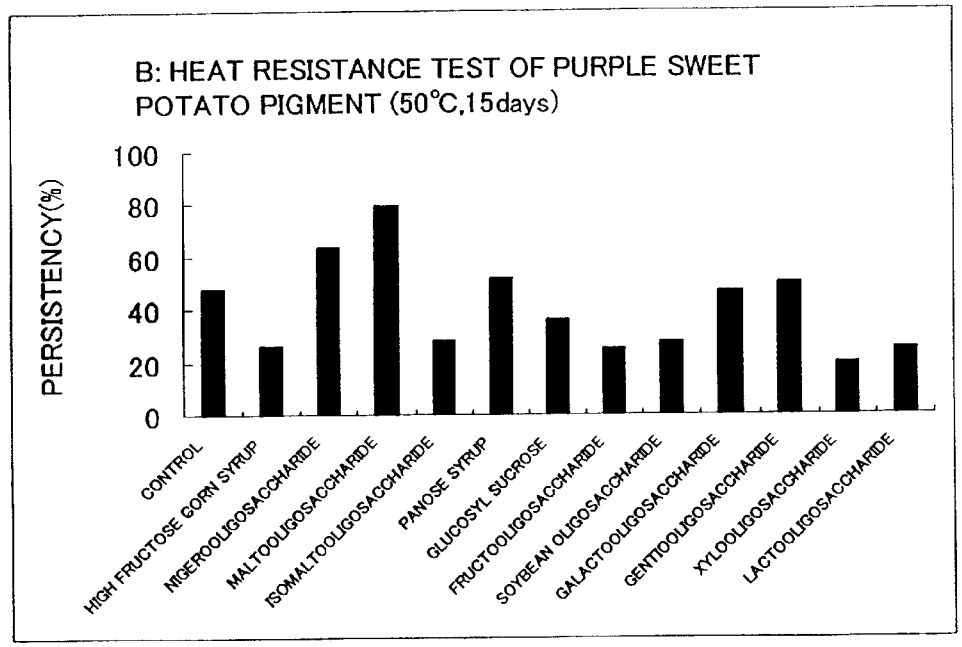

FIG. 14 LIGHT RESISTANCE OF PURPLE CORN PIGMENT
A: IRRADIATION FOR 4 HOURS USING FADE-METER
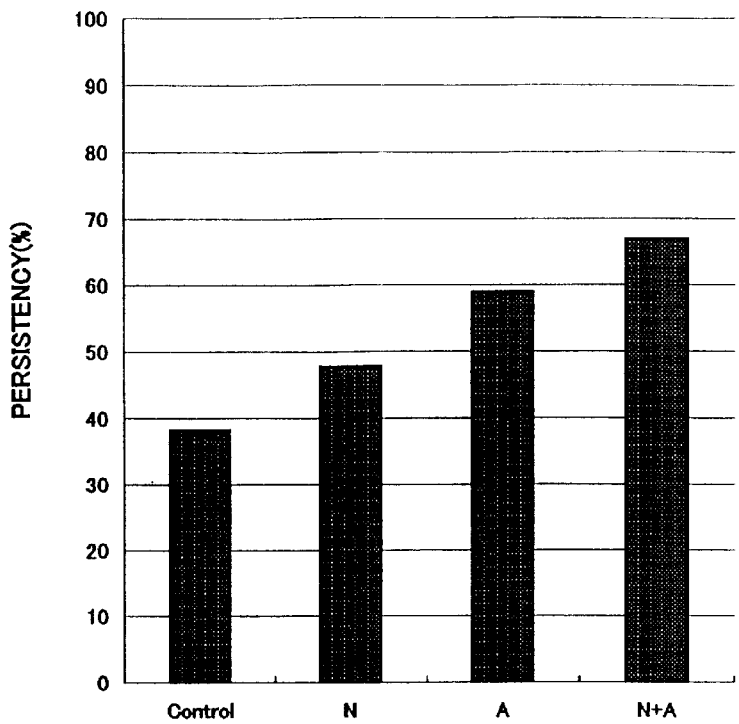
B: IRRADIATION FOR 72 HOURS USING ENVIRONMENT CONTROLLER
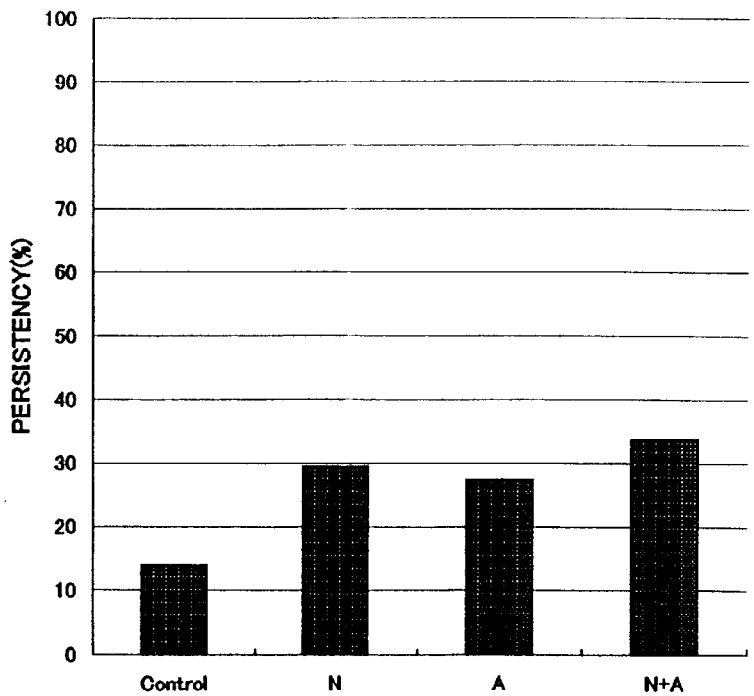
N: WHEN NIGEROOLIGOSACCHARIDE (1%) IS ADDED
A: WHEN ANTIOXIDANT (0.05%) IS ADDED
N+A: WHEN NIGEROOLIGOSACCHARIDE (1%) AND ANTIOXIDANT (0.05%) ARE ADDED FIG. 15 LIGHT RESISTANCE OF RED CABBAGE PIGMENT
A: IRRADIATION FOR 4 HOURS WITH USING FADE-METER
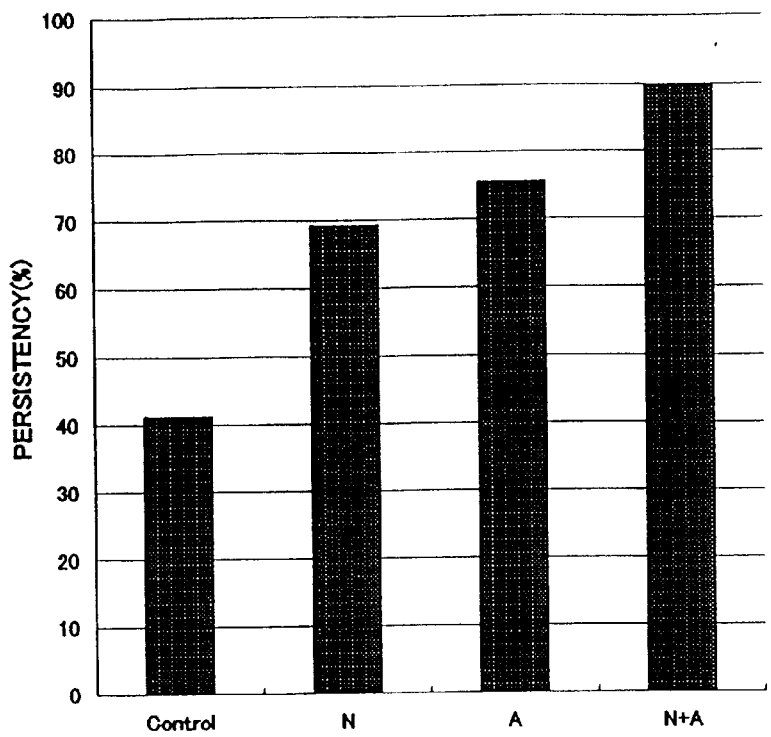
B: IRRADIATION FOR 72 HOURS USING ENVIRONMENT CONTROLLER
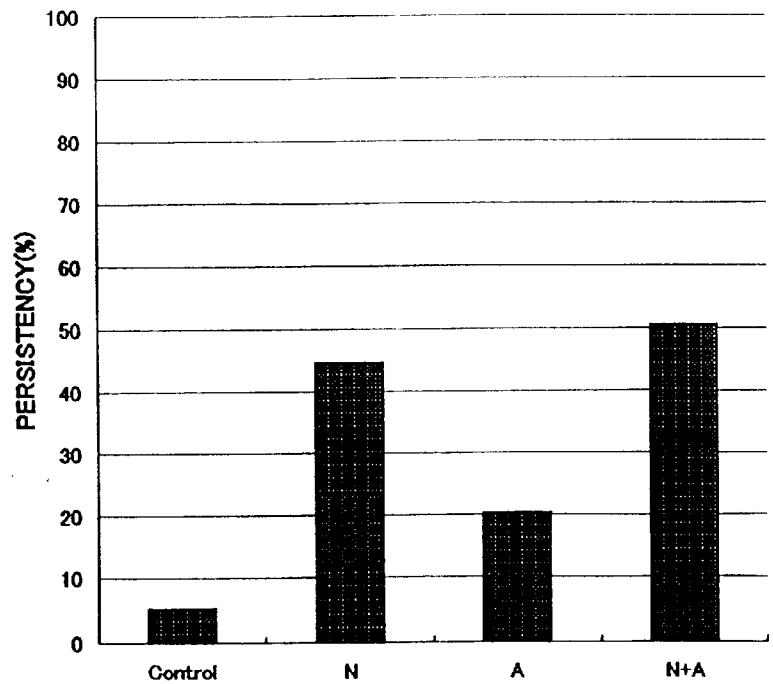
N: WHEN NIGEROOLIGOSACCHARIDE (1%) IS ADDED
A: WHEN ANTIOXIDANT (0.05%) IS ADDED
N+A: WHEN NIGEROOLIGOSACCHARIDE (1%) AND ANTIOXIDANT (0.05%) ARE ADDED FIG. 16 LIGHT RESISTANCE OF PURPLE SWEET POTATO PIGMENT
A: IRRADIATION FOR 4 HOURS USING FADE-METER
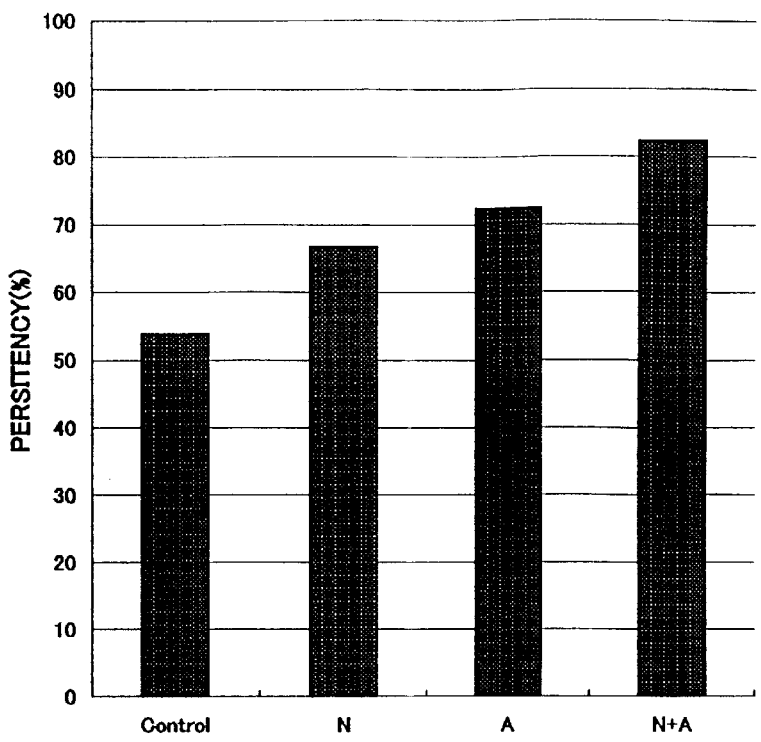
B: IRRADIATION FOR 72 HOURS USING ENVIRONMENT CONTROLLER
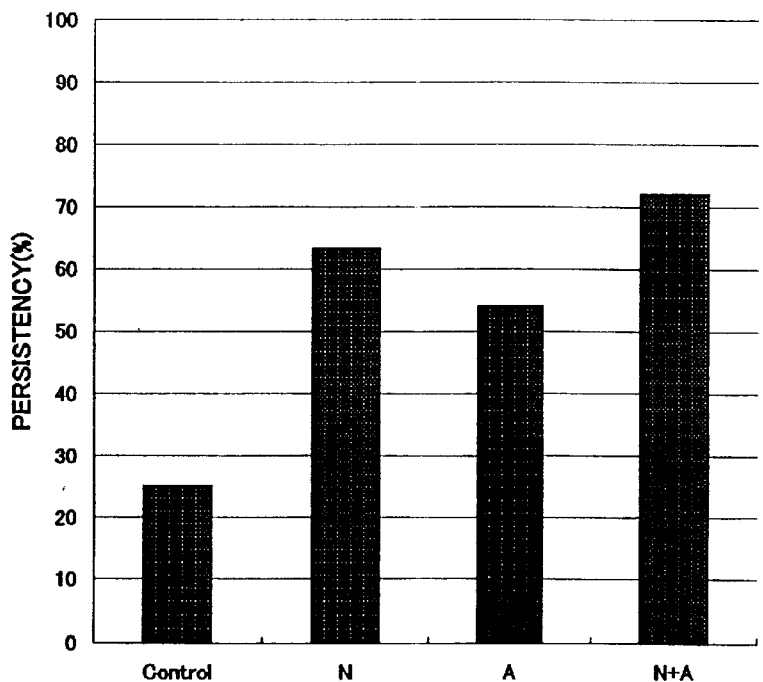
N: WHEN NIGEROOLIGOSACCHARIDE (1%) IS ADDED
A: WHEN ANTIOXIDANT (0.05%) IS ADDED
N+A: WHEN NIGEROOLIGOSACCHARIDE (1%) AND ANTIOXIDANT (0.05%) ARE ADDED FIG. 17 LIGHT RESISTANCE OF GARDENIA RED PIGMENT
A: IRRADIATION FOR 6 HOURS USING FADE-METER
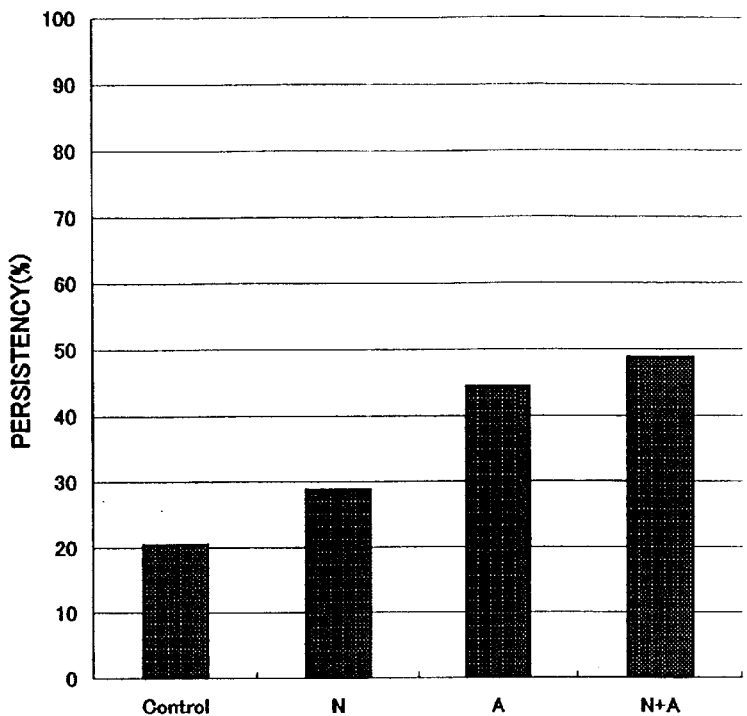
B: IRRADIATION FOR 72 HOURS USING ENVIRONMENT CONTROLLER
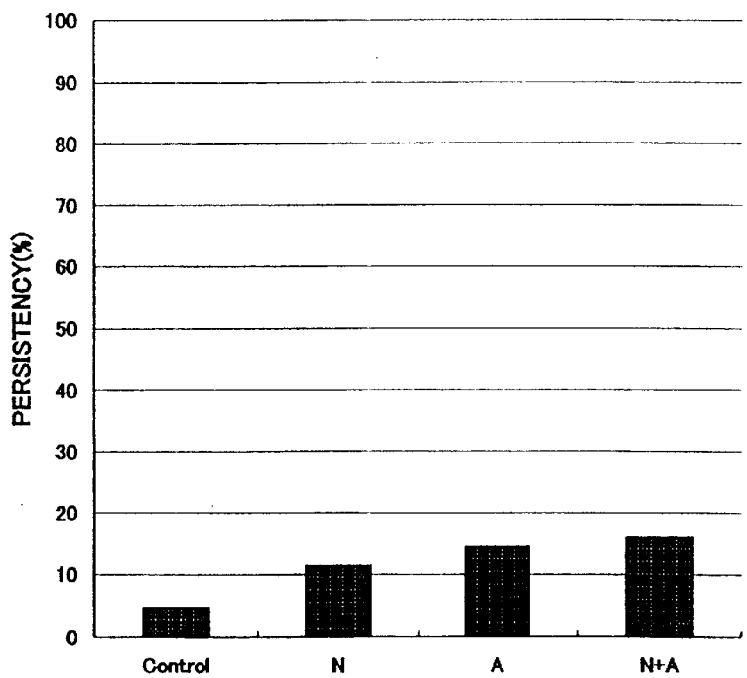
N: WHEN NIGEROOLIGOSACCHARIDE (1%) IS ADDED
A: WHEN ANTIOXIDANT (0.05%) IS ADDED
N+A: WHEN NIGEROOLIGOSACCHARIDE (1%) AND ANTIOXIDANT (0.05%) ARE ADDED FIG. 18 LIGHT RESISTANCE OF COCHINEAL PIGMENT
A: IRRADIRATION FOR 4 HOURS USING FADE-METER
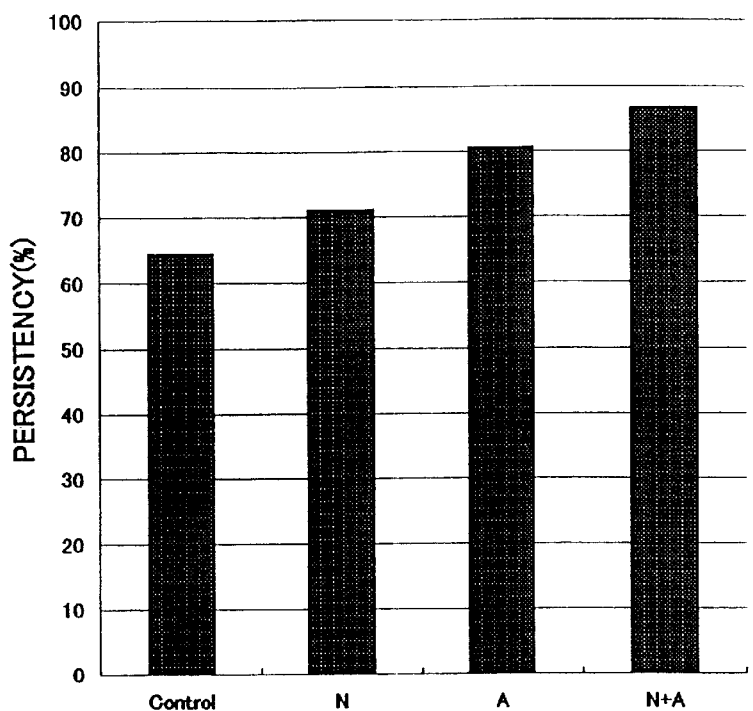
B: IRRADIATION FOR 72 HOURS USING ENVIRONMENT CONTROLLER
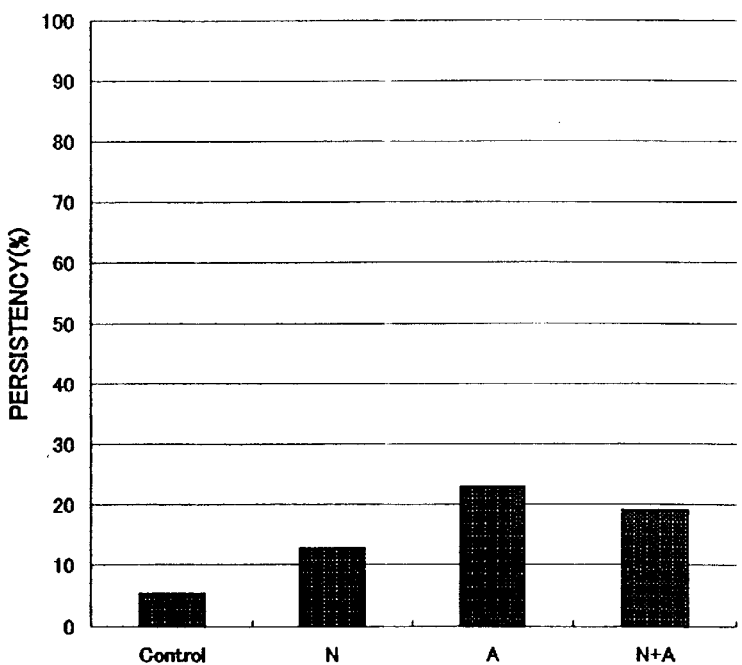
N: WHEN NIGEROOLIGOSACCHARIDE (1%) IS ADDED
A: WHEN ANTIOXIDANT (0.05%) IS ADDED
N+A: WHEN NIGEROOLIGOSACCHARIDE (1%) AND ANTIOXIDANT (0.05%) ARE ADDED LIGHT RESISTANCE OF GARDENIA BLUE PIGMENT
(IRRADIATION FOR 4 HOURS USING FADE-METER)

N: WHEN NIGEROOLIGOSACCHARIDE (1%) IS ADDED
A: WHEN ANTIOXIDANT (0.05%) IS ADDED
N+A: WHEN NIGEROOLIGOSACCHARIDE (1%) AND ANTIOXIDANT (0.05%) ARE ADDED

LIGHT RESISTANCE OF CARTHAMUS YELLOW PIGMENT (LIGHT IRRADIATION FOR 8 HOURS USING FADE-METER)

N: WHEN NIGEROOLIGOSACCHARIDE (1%) IS ADDED
A: WHEN ANTIOXIDANT (0.05%) IS ADDED
N+A: WHEN NIGEROOLIGOSACCHARIDE (1%) AND ANTIOXIDANT (0.05%) ARE ADDED

LIGHT RESISTANCE TEST OF PURPLE CORN PIGMENT
(IRRADIATION WITH FLUORESCENT RAY)

METHOD FOR INHIBITING FADING OF A NATURAL PIGMENT USING NIGEROOLIGOSACCHARIDE OR MALTOOLIGOSACCHARIDE OR PANOSE WITH OR WITHOUT AN ANTIOXIDANT

TECHNICAL FIELD

The present invention relates to an anti-fading agent. More specifically, the present invention relates to a anti-fading agent capable of advantageously inhibiting fading in colors of pigments caused by light, heat or the like, by comprising a specific oligosaccharide as an active ingredient. Further, the present invention relates to beverage and food products that are significantly suppressed in fading in colors by containing the anti-fading agent.

BACKGROUND ART

Conventionally, various synthetic pigments and natural pigments are used for coloring beverage and food products. In recent years, the natural pigments have been widely used, especially since safety of the synthetic pigments was called into question.

However, the natural pigments are comparatively unstable and tend to fade or change in colors with time as being affected by light, oxygen, heat and the like. Therefore the products such as beverage and food products, cosmetics and medicines by the natural pigments have problems that their commercial values would be reduced remarkably by suffering from the fading or change in colors. Since beverages bottled in clear container such as PET bottles are prevailed and products reduced in degree of coloring are preferred particularly in recent days, there is a demand for immediately developing a method for advantageously suppressing or preventing the pigments from fading in colors.

DISCLOSURE OF THE INVENTION

An object of the present invention is to provide an anti-fading agent capable of advantageously suppressing fading in colors of pigments. Another object of the present invention is to provide an anti-fading agent effective against fading in colors caused particularly by heat and light.

Another object of the invention is to provide colored beverage and food products which are significantly suppressed in fading in colors of pigments by containing the anti-fading agent.

Note that the word "fading in colors" used herein includes reduction in coloring strength (of the degree of coloring) and change in colors of pigments.

The inventors have carried out an extensive research to achieve the above objects, and found specific oligosaccharides such as nigerooligosaccharide, maltooligosaccharide and panose exert an excellent suppressing or inhibitory action on fading in colors of various pigments, especially of natural pigments. The inventors have studied further based on the findings and succeeded in improving the above-described anti-fading action of the oligosaccharides by using them together with an antioxidant, to thereby accomplish the present invention.

The present invention provides an anti-fading agent for pigments, comprising at least one oligosaccharide-selected from the group consisting of nigerooligosaccharide, maltooligosaccharide and panose as an active ingredient.

Further, the present invention provides an anti-fading agent for pigments, comprising at least one oligosaccharide selected from the group consisting of nigerooligosaccharide, maltooligosaccharide and panose and an antioxidant as active ingredients.

In addition, in the anti-fading agent of the present invention, the following embodiments may be included.
(1) An anti-fading agent for a pigment wherein the pigment is a natural pigment.
(2) An anti-fading agent for a pigment wherein the pigment is at least one natural pigment selected from the group consisting of quinoid-based pigments, anthocyanin-based pigments, flavonoid-based pigments, azaphilone-based pigments, betacyanin-based pigments, Gardenia blue pigment and Gardenia red pigment.
(3) An anti-fading agent for a pigment, wherein the pigment is an anthocyanin-based pigment.
(4) An anti-fading agent for a pigment, wherein the pigment is a carotinoid-based pigment or a flavonoid-based pigment.
(5) An anti-fading agent for a pigment, which comprises at least one antioxidant selected from the group consisting of Chinese bayberry extract, rutin extract, coffee bean extract, rosemary extract, enzymatically modified rutin and enzymatically modified isoquercitrin.

Further, the present invention provides a pigment-containing colored substance which is suppressed in fading in colors by containing above-described anti-fading agent comprising the oligosaccharide or the oligosaccharide and antioxidant as active ingredients. The following embodiments may be included in the pigment-containing colored substance.
(a) A pigment-containing colored substance, wherein the colored substance is a beverage and food product.
(b) A pigment-containing colored substance, wherein the pigment is a natural pigment.
(c) A pigment-containing colored substance, wherein the pigment is at least one natural pigment selected from the group consisting of quinoid-based pigments, anthocyanin-based pigments, flavonoid-based pigments, azaphilone-based pigments, betacyanin-based pigments, Gardenia Blue pigment and Gardenia Red pigment.
(d) A pigment-containing colored substance, wherein the pigment is an anthocyanin-based pigment.
(e) A pigment-containing colored substance, wherein the pigment is a carotinoid-based pigment or a flavonoid-based pigment.
(f) A pigment-containing colored substance which comprises the anti-fading agent in an amount of at least 0.1 parts by weight calculated as an oligosaccharide content.
(g) A pigment-containing colored substance which comprises 0.5–100 parts by weight of the antioxidant based on 100 parts by weight of the oligosaccharide contained therein.
(h) A pigment-containing colored substance, which comprises at least one antioxidant selected from the group consisting of Chinese bayberry extract, rutin extract, coffee bean extract, rosemary extract, enzymatically modified rutin and enzymatically modified isoquercitrin.

Further, the present invention provides a method for inhibiting fading in colors of the pigment, wherein above-described anti-fading agent comprising as active ingredients the oligosaccharide or the oligosaccharide and antioxidant is added to a pigment. The following embodiments may be included in the method for inhibiting fading in colors.
(i) A method for inhibiting fading in colors of the pigment, wherein the pigment is a natural pigment.
(ii) A method for inhibiting fading in colors of the pigment, wherein the pigment is at last one natural pigment selected from the group consisting of quinoid-based pigments, anthocyanin-based pigments, flavonoid-based pigments, azaphilone-based pigments, betacyanin-based pigments, Gardenia Blue pigment and Gardenia Red pigment.

(iii) A method for inhibiting fading in colors of the pigment, wherein the pigment is an anthocyanin-based pigment.

(iv) A method for inhibiting fading in colors of the pigment, wherein the pigment is a carotinoid-based pigment or a flavonoid-based pigment.

(v) A method for inhibiting fading in colors of the pigment, wherein the fading in colors is caused by light irradiation.

(vi) A method for inhibiting fading in colors of the pigment, wherein the fading in colors is caused by heat-treatment.

BRIEF DESCRIPTION OF DRAWINGS

FIG. 11 shows anti-fading effects of the subject sugars on the red cabbage pigment (Experiment 4). FIG. A shows the anti-fading effects against light irradiation (light-resistance), and FIG. B shows the anti-fading effects against heat (heat-resistance).

FIG. 12 shows anti-fading effects of the subject sugars on the purple sweet potato pigment (Experiment 4). FIG. A shows the anti-fading effects against light irradiation (light-resistance), and FIG. B shows the anti-fading effects against heat (heat-resistance).

FIG. 14 shows anti-fading effects (light-resistance) of nigerooligosaccharide and of nigerooligosaccharide and an antioxidant on the purple corn pigment (Experiment 5). FIG. A shows the anti-fading effects against irradiation with ultraviolet rays, and FIG. B shows the anti-fading effects against irradiation with fluorescent rays.

FIG. 15 shows anti-fading effects (light-resistance) of nigerooligosaccharide and of nigerooligosaccharide and an antioxidant on the red cabbage pigment (Experiment 5). FIG. A shows the anti-fading effects against irradiation with ultraviolet rays, and FIG. B shows the anti-fading effects against irradiation with fluorescent rays.

FIG. 16 shows anti-fading effects (light-resistance) of nigerooligosaccharide and of nigerooligosaccharide and an antioxidant on the purple sweet potato pigment (Experiment 5). FIG. A shows the anti-fading effects against irradiation with ultraviolet rays, and FIG. B shows the anti-fading effects against irradiation with fluorescent rays.

FIG. 17 shows anti-fading effects (light-resistance) of nigerooligosaccharide and of nigerooligosaccharide and an antioxidant on the Gardenia Red pigment (Experiment 5). FIG. A shows the anti-fading effects against irradiation with ultraviolet rays, and FIG. B shows the anti-fading effects against irradiation with fluorescent rays.

FIG. 18 shows anti-fading effects (light-resistance) of nigerooligosaccharide and of nigerooligosaccharide and an antioxidant on the cochineal pigment (Experiment 5). FIG. A shows the anti-fading effects against irradiation with ultraviolet rays, and FIG. B shows the anti-fading effects against irradiation with fluorescent rays.

BEST MODE FOR CARRYING OUT THE INVENTION

Figure 1:
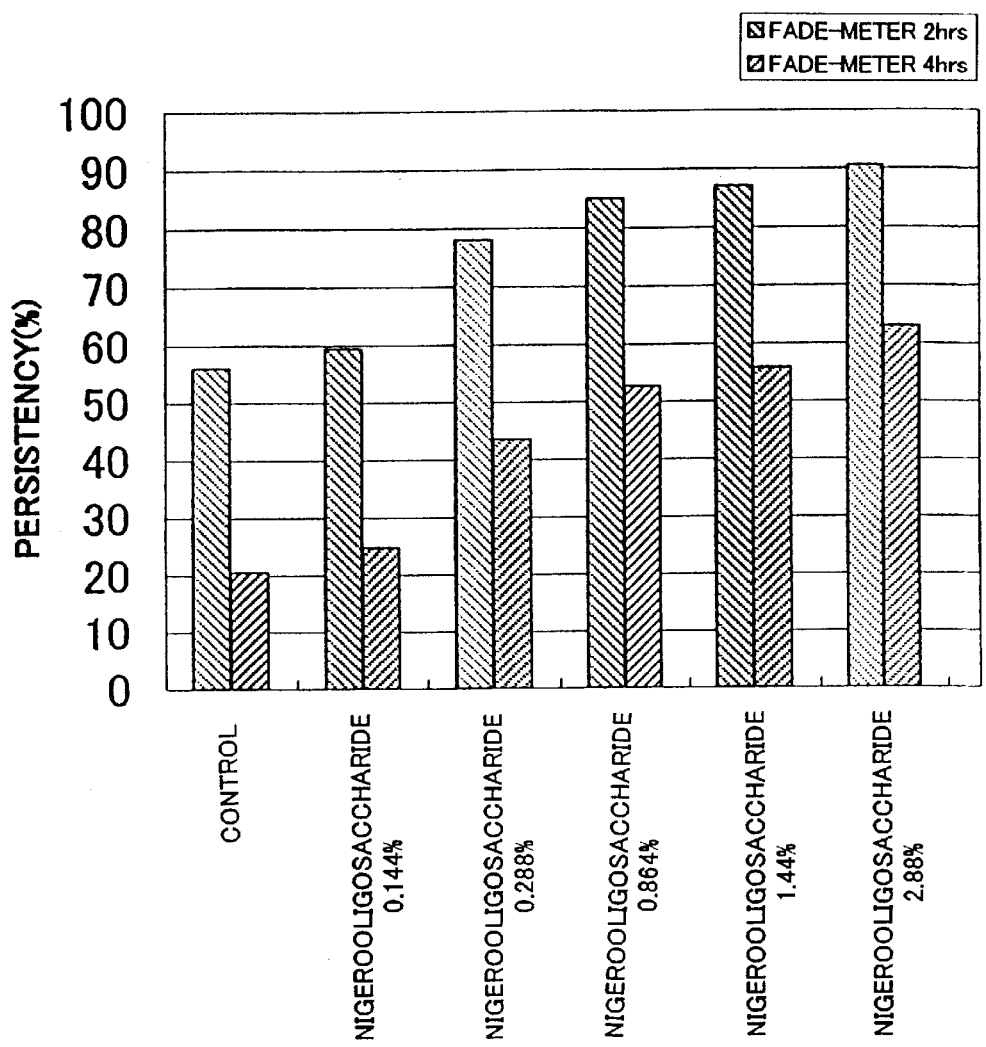
FIG. 1 shows a light-resistance effect (anti-fading effect) of the anti-fading agent (nigerooligosaccharide) of the present invention on the red cabbage pigment (Experiment 1).
Figure 2:
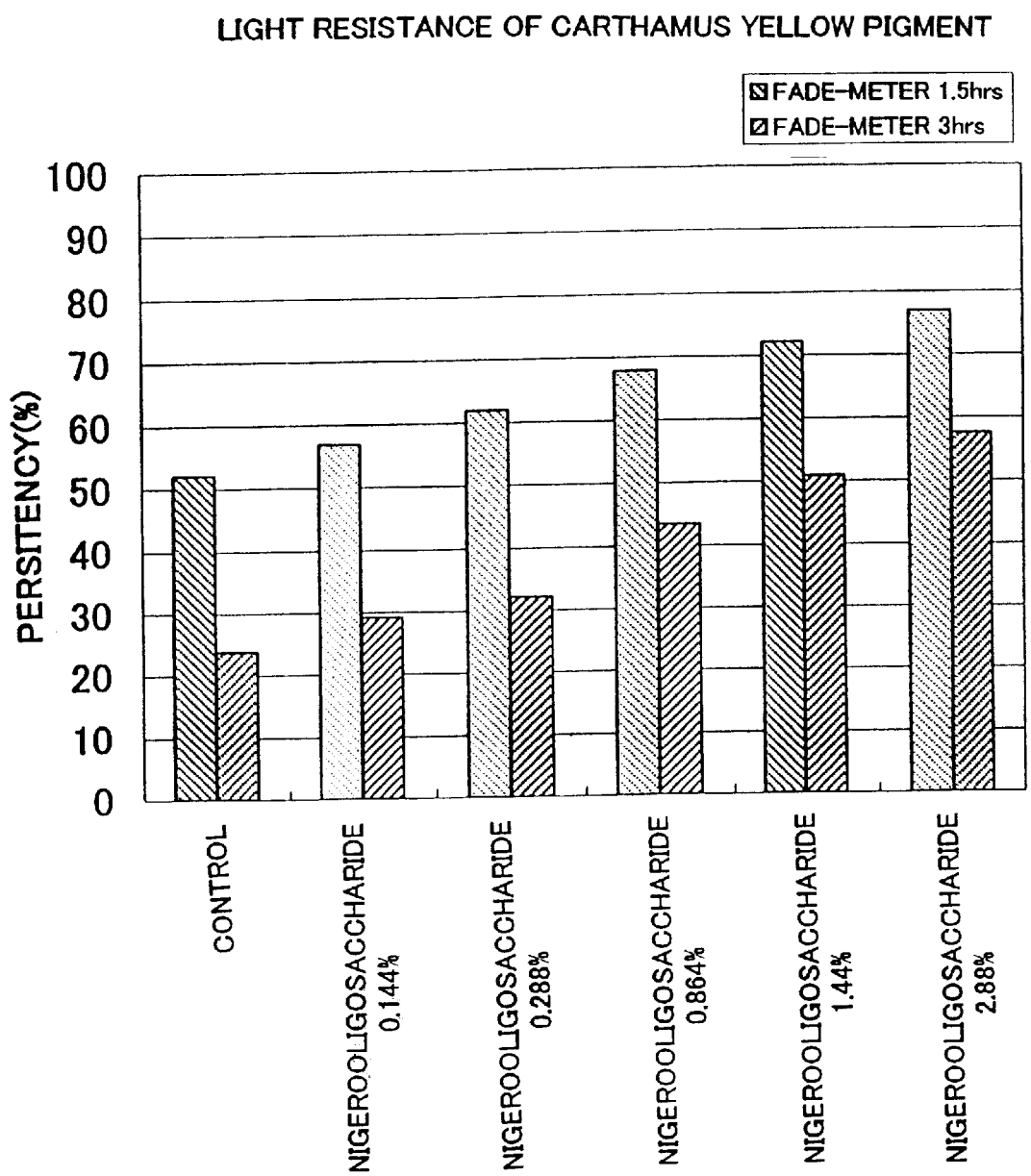
FIG. 2 shows a light-resistance effect (anti-fading effect) of the anti-fading agent (nigerooligosaccharide) of the present invention on the Carthamus yellow pigment (Experiment 1).
Figure 3:
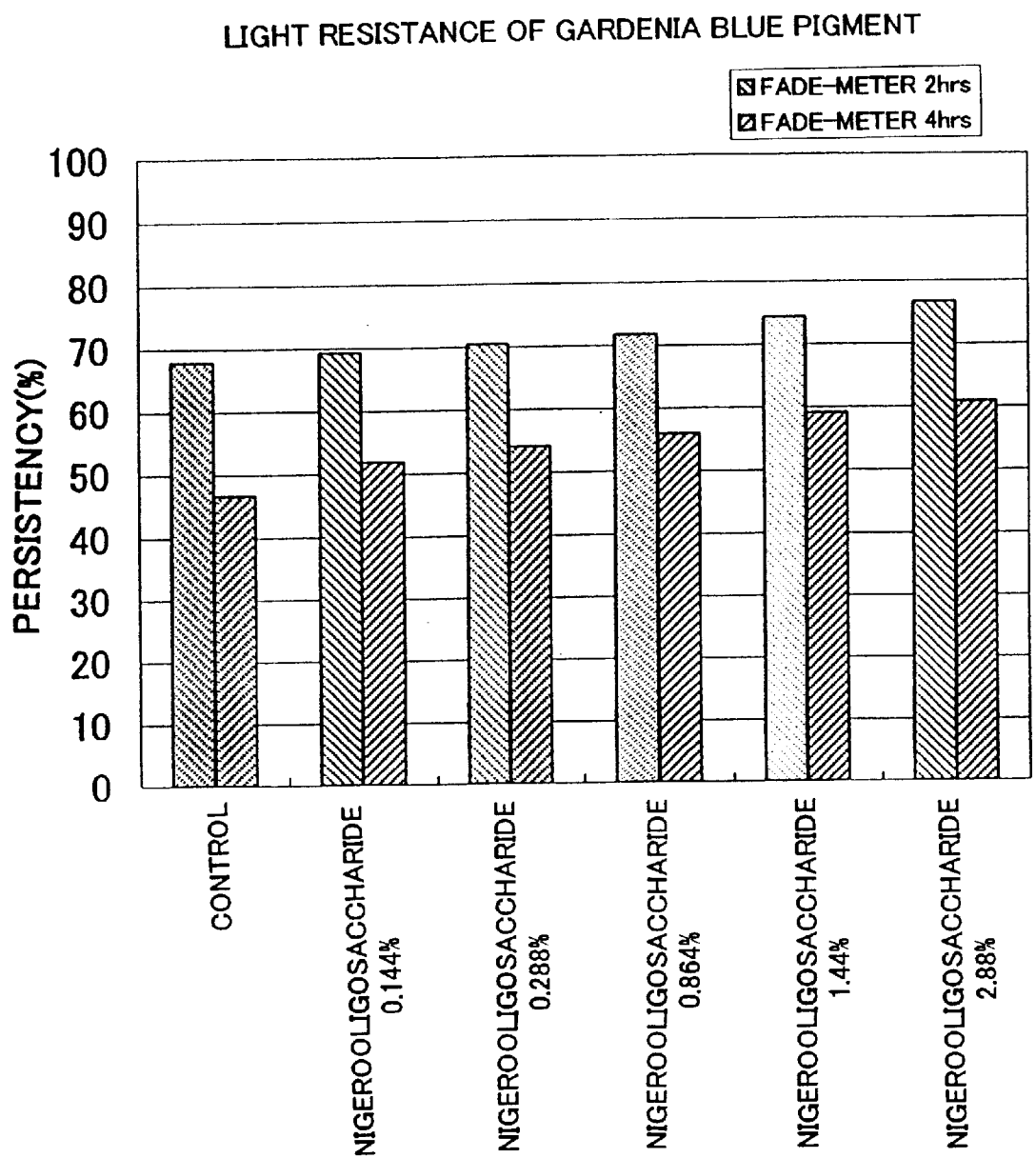
FIG. 3 shows a light-resistance effect (anti-fading effect) of the anti-fading agent (nigerooligosaccharide) of the present invention on the Gardenia Blue pigment (Experiment 1).
Figure 4:
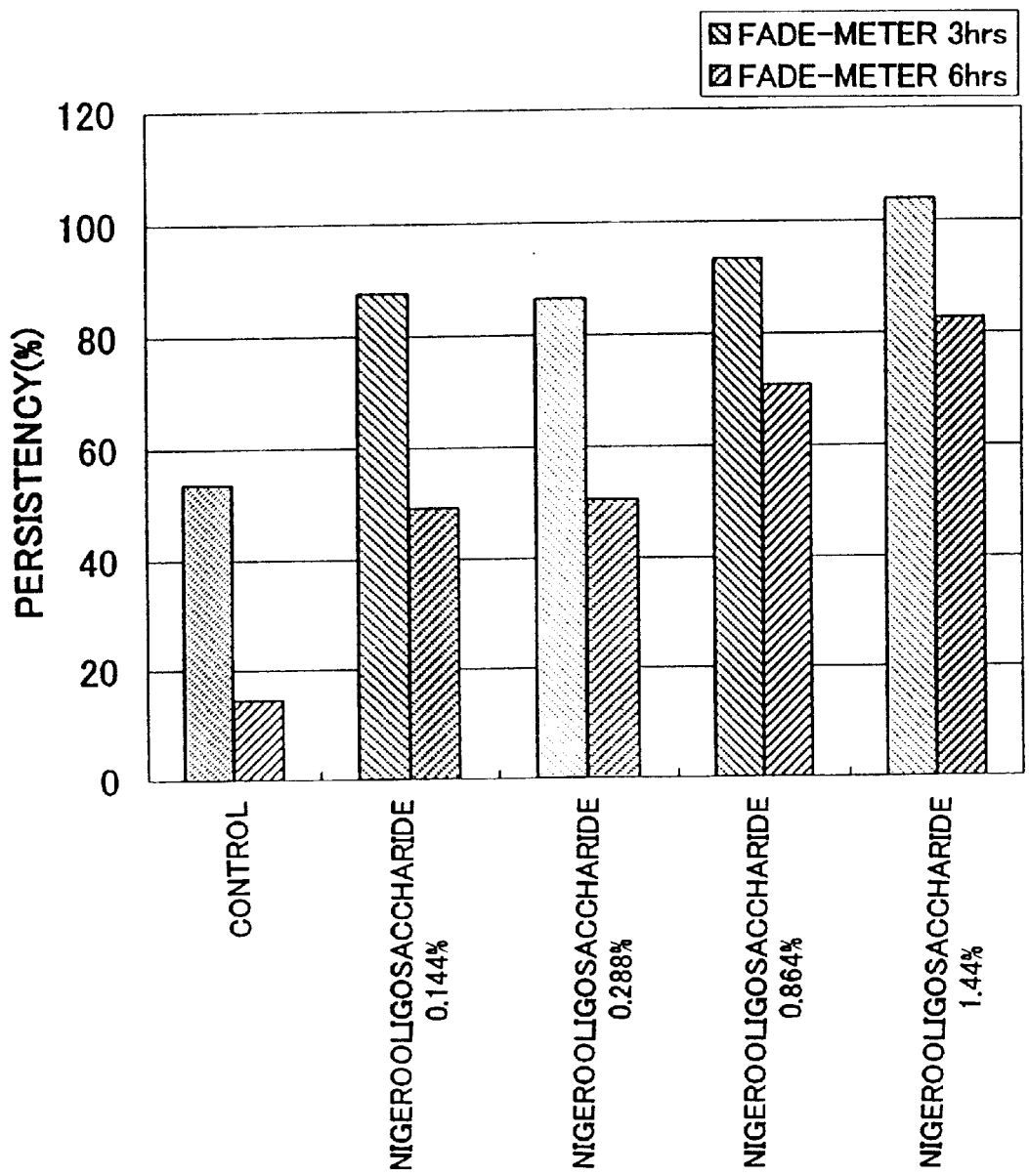
FIG. 4 shows a light-resistance effect (anti-fading effect) of the anti-fading agent (nigerooligosaccharide) of the present invention on the purple sweet potato pigment (Experiment 1).
Figure 5:
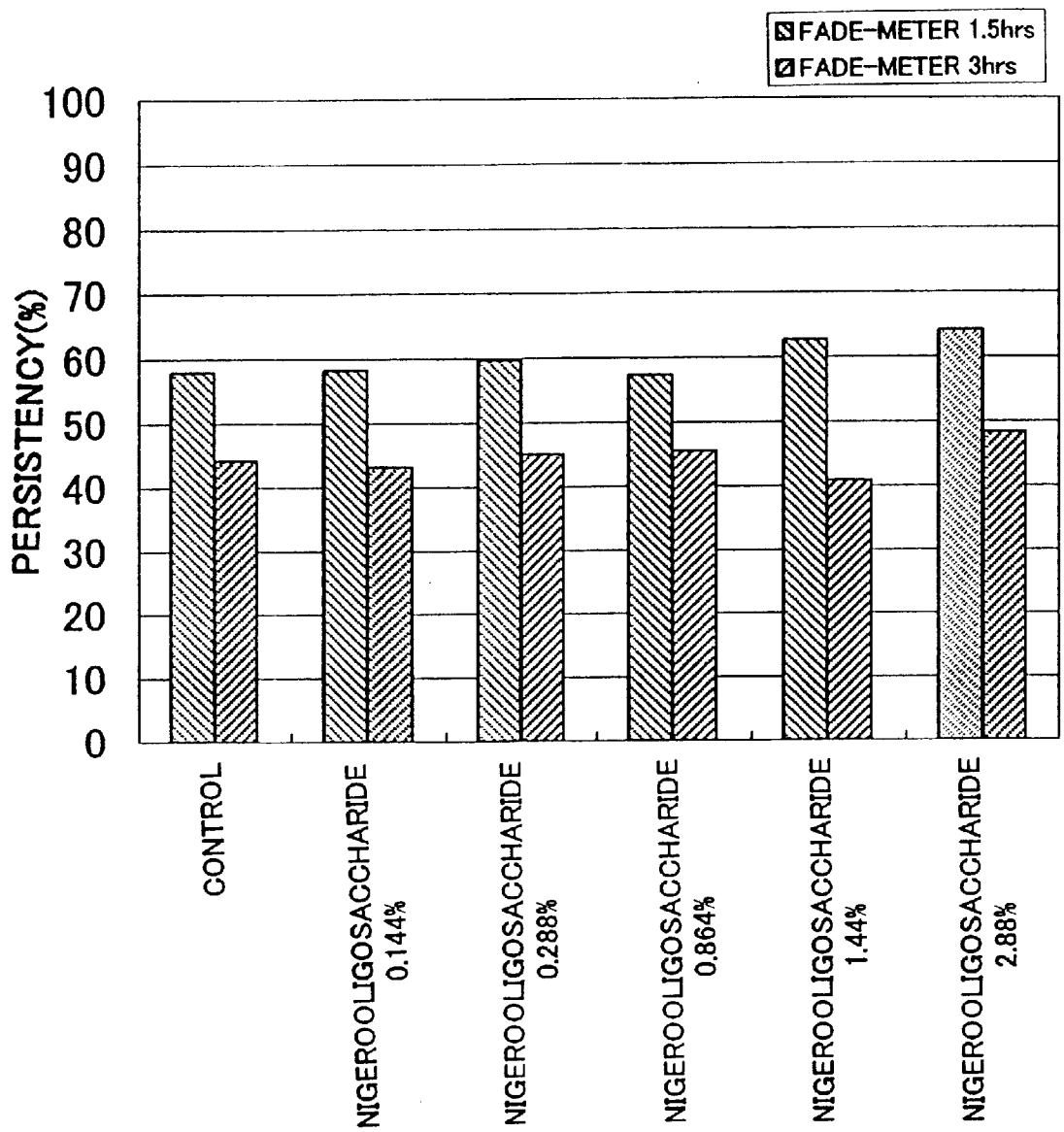
FIG. 5 shows a light-resistance effect (anti-fading effect) of the anti-fading agent (nigerooligosaccharide) of the present invention on the purple corn pigment (Experiment 1).

The anti-fading agent of the present invention comprises a specific oligosaccharide, specifically nigerooligosaccharide, maltooligosaccharide or panose as an active ingredient.

As used herein, "nigerooligosaccharide" means oligosaccharides with a degree of glucose polymerization of about 2 or more and containing an $\alpha$-1,3-glucoside linkage. Such nigerooligosaccharide may contain at least one $\alpha$-1,3-glucoside linkage. Examples of the nigerooligosaccharide include oligosaccharides comprising only the $\alpha$-1,3-glucoside linkage and oligosaccharides comprising the $\alpha$-1,3-glucoside linkage and another linkage (e.g. $\alpha$-1,4-glucoside linkage). Specific examples of the nigerooligosaccharide are nigeronigerose, nigerosylglucose, nigerosylmaltose and so on, which may be used for the anti-fading agent of the invention solely or in combination of 2 or more.

The nigerooligosaccharide is not particularly limited, but is obtainable by known preparation processes such as, for example, a process employing a hydrolysis of nigeran, erucinan or the like using an enzyme or an acid (Methods in Carbohydrate Chemistry, I, 339–341, Academic Press 1962), a process employing transglycosylation and/or condensation reaction of α-glucosidase (Japanese Unexamined Patent Publication No. 299095/1997), a process wherein a cyclodextrin-forming enzyme is allowed to act on a starch hydrolyzate (Japanese Unexamined Patent Publication No. 22958/1991), and a process wherein a glycosyltrancsferase is allowed to act on polysaccharide and the like (Japanese Unexamined Patent Publication No. 59559/1995).

From the viewpoints of yields and economy, the process described in the Japanese Unexamined Patent Publication No. 299095/1997 is preferred. In the process, nigerooligosaccharide is obtainable as a syrup containing not less than 30 wt. % of nigerooligosaccharide in the solid sugar content by allowing an enzyme which generates nigerooligosaccharide upon transglycosylation and/or condensation reaction to act on a substrate comprising an aqueous sugar solution containing in a solid sugar content not less than 50 wt. % of sugar with a degree of glucose polymerization of 2 or more, to thereby generate. In addition, examples of the aqueous sugar solution include aqueous solutions prepared by allowing at least one enzyme selected from α-amylase, β-amylase, oligosaccharide-generating amylase and dedranching enzyme to act on a gelatinized starch.

As described above, nigerooligosaccharide to be used in the invention is not necessarily be a pure nigerooligosaccharide, but may be used in the form of a syrup containing nigerooligosaccharide which is obtainable by the process disclosed in the Japanese Unexamined Patent Publication No. 299095/1997 or like processes according to the use application. A nigerooligosaccharide content in the syrup is not limited, and may be about 30 wt. % or more per solid content. In addition, it is possible to increase the nigerooligosaccharide content by purifying the syrup as required. Examples of the purification method include a method of precipitating oligosaccharides by adding an organic solvent such as alcohol to the syrup, a method wherein various chromatography such as adsorption and gel filtration are employed, a method of degrading a fermentable sugar chain by adding yeast to the syrup, and the like.

As used herein, "maltooligosaccharide" means oligosaccharides, which are starch hydrolyzates, with a degree of glucose polymerization of 2–10 and comprising linear α-1,4-glucosidic linkages. Examples of the maltooligosaccharide include maltose (having a degree of polymerization 2: G2), maltotriose (G3), malttetraose (G4), maltopentaose (G5), maltohexaose (G6), maltoheptaose (G7), maltooctaose (G8), maltononaose (G9) and maltodecaose (G10). These maltooligosaccharides may be used solely or in combination of 2 or more. From the viewpoints of water-solubility and heat stability, it is preferred to use maltooligosaccharides with a degree of polymerization of not less than 3, in particular not less than 4. In addition, these maltooligosaccharides can be prepared by partially decomposing a starch or amylose with an α-amylase or an acid or by using a microorganism-derived enzyme which specifically generates maltooligosaccharides. Commercially available maltooligosaccharides may simply be used in the invention.

As used herein, panose is an aqueous reducing trisaccharide comprising a D-glucose termolecular linked at the nonreducing terminal by α-1,6 linkages and α-1,4 linkages. It is possible to prepare the panose by a process such as a process wherein maltose is allowed to act on a transferase derived from *Aspergillus niger*, a process wherein a transferase derived from *Leuconostoc* is allowed to act on sucrose and maltose and a process wherein amylopectin or glycogen is subjected to a partial hydrolysis. Also, a commercially available panose can be used in the invention. In addition, these panose may be used solely or in combination of 2 or more in the invention.

The anti-fading agent of the present invention may contain at least one oligosaccharide selected from the above-described nigerooligosaccharide, maltooligosaccharide and panose. The anti-fading agent may comprise the oligosaccharide or a syrup containing the oligosaccharide. Further, the anti-fading agent may be a composition composed of other ingredients such as a diluent, carrier or other additives. The diluent, carrier and additives are not limited insofar as they do not inhibit the advantageous effect of the present invention, and examples of which includes sucrose, glucose, dextrin, arabia gum, water, starch syrup, ethanol, propyleneglycol, glycerin and the like.

Ingredients for supporting or enhancing anti-fading action of the oligosaccharide may be added to the anti-fading agent of the present invention, and suitable examples of which include an antioxidant, etc.

Various antioxidants may be used in the invention insofar as they are usable as food additives, and examples of which include, but not limited to, ascorbic acids such as L-ascorbic acid and salts thereof, erysorbic acids such as erysorbic acid and salts thereof; sulfites such as sodium sulfite and potassium pyrosulfite; tocopherols such as α-tocopherol and mixed tocopherol; dibutylhydroxytoluene (BHT), butylhydroxyanisole (BHA) and the like; ascorbic acid esters such as ascorbic acid palmitic acid ester; various plant extracts such as a Hollyhock flower extract, licorice oil extract, edible canna extract, clove extract, apple extract, Essential oil-removed fennel extract, horseradish extract, sage extract, dropwort (Oenanthe javanica) extract, tea (leaf) extract, Dokudami extract, coffee bean extract, sunflower seed extract, pimento extract, grape seed extract, blueberry leaf extract, Hego-Gingo leaf extract, pepper extract, Garden balsam extract, Chinese bayberry extract, eucalyptus leaf extract, gentiana root extract, rutin extract (Azuki extract, Enju extract, buckwheat extract), rosemary extract and the like as well as Enzymatically modified rutin, Enzymatically decomposed rutin (quercetin), Enzymatically modified isoquercitrin, rapeseed oil extract, rice bran oil extract, Enzymatically decomposed rice bran, gallic acid and esters thereof.

Preferred examples of the antioxidants include the Chinese bayberry extract, rutin extract, coffee bean extract, rosemary extract and like plant extracts; enzymatically modified rutin, enzymatically modified isoquercitrin, and the like.

Proportion of the antioxidant to be comprised in the anti-fading agent is not limited insofar as the proportion is effective for enhancing the anti-fading action of the oligosaccharides, and may be selected and adjusted depending on type of an object pigment and types of oligosaccharide and antioxidant to be employed. The proportion of the antioxidant may be, based on 100 parts by weight of the oligosaccharide comprised in the anti-fading agent, typically 0.5–100 parts by weight, preferably 1–20 parts by weight and more preferably 5–10 parts by weight.

Form of the anti-fading agent of the invention is not limited, but may be prepared in the form of a powder, granulate, tablet, liquid, emulsion, paste and the like.

The anti-fading agent may be used for various types of pigments irrespective of whether it is synthetic or natural.

Examples of the synthetic pigments include coaltar pigments such as Acid Red 27, Acid Red 51, Food Red 17, Acid Red 18, Acid Red 92, Acid Red 94, Acid Red 52, Acid Yellow 23, Food Yellow 3, Acid Blue 9, Acid Blue 74 and Food Green 3; inorganic pigments such as sesquioxide and titanium dioxide; natural pigment derivatives such as Disodium norbixinate, Dipotassium norbixinate, copper chlorophyll, copper chlorophyllin Na and iron chlorophyllin Na; and synthetic natural pigments such as β-carotene, riboflavin, riboflavin tetrabutyrate, riboflavin 5'-phosphate sodium, Orange B, Citrus Red No. 2, Quinoline Yellow, Red 2G, Patent Blue, Green S, Brilliant Black BN, Black PN, Brown FK, Brown HT, Lithol Rubin BK, riboflavin-5'-phosphate and copper chlorophyllin. Examples of the natural pigments include carotenoid-based pigments such as annatto extract, Gardenia yellow, dunaliella carotene, carrot carotene, palm oil carotene, tomato pigment, paprika pigment, canthaxanthin, β-apo-8'-carotenal and β-apo-8'-catotenic acid ethylester; quinoid-based pigments such as madder pigment, cochineal extract, Shikon pigment and Lac color; anthocyanin-based pigment such as red cabbage pigment, perilla pigment, hibiscus pigment, grape juice pigment, grape skin pigment, purple sweet potato pigment, purple corn pigment, elderberry pigment and boysenberry pigment; flavonoid-based pigments such as cacao pigment, kaoliang pigment, Sandalwood red pigment, onion pigment, tamarind pigment, Japanese persimmon pigment, carob germ pigment, licorice pigment, sappan wood pigment, Carthamus red pigment and Carthamus yellow pigment; porphyrin-based pigments such as chlorophyllin pigment, chlorophyll and spirulina pigment; diketone-based pigments such as turmeric pigment; azaphilone-based pigments such as monascus pigment, betacyanin-based pigments such as beet red; Monascus Yellow pigment; caramel; Gardenia Blue; Gardenia Red; gold; silver; aluminium-based pigments and the like.

The anti-fading agent of the invention may preferably be used for natural pigments and, in particular, may suitably be used for various pigments belonging to carotenoid-based, anthocyanin-based, flavonoid-based, betacyanin-based, quinoid-based and azaphilone-based pigments as well as for Gardenia Blue pigment and Gardenia Red pigment. The anti-fading agent of the invention is particularly excellent in suppressing fading in colors caused by light of carotenoid-based pigments, anthocyanin-based pigments, flavonoid-based pigments, azaphilone-based pigments, quinoid-based pigments, Gardenia Red pigment and Gardenia Blue pigment, especially in suppressing fading in colors caused by light (light-resistance) of the carotenoid-based pigments, flavonoid-based pigments and Gardenia Blue pigment, more preferably of the anthocyanin-based pigments.

The anti-fading agent of the invention is excellent in suppressing fading in colors by heat of carotenoid-based pigments, anthocyanin-based pigments, flavonoid-based pigments, betacyanin-based pigments, azaphilone-based pigments and Gardenia Blue pigment, in particular of the anthocyanin-based pigments.

Therefore, the anti-fading agent of the invention is applicable for various substances containing the pigments mentioned above and useful for suppressing or preventing the fading in colors of the substances. Examples of the substances include beverage and food products, cosmetics, pharmaceuticals, quasi-drugs, fodder and the like.

Thus, the present invention provides colored beverage and food products, cosmetics, pharmaceuticals quasi-drugs and fodder which are significantly suppressed in fading in colors of pigments by containing an anti-fading agent comprising at least one oligosaccharide selected from nigerooligosaccharide, maltooligosaccharide and panose or a anti-fading agent comprising the antioxidant in addition to the oligosaccharide.

Examples of the cosmetics include, but not limited to, skin lotion, lipsticks, cosmetics for sunscreen, cosmetics for makeup and the like. Examples of the pharmaceuticals include, but not limited to, various types of tablets, capsules, ampuled liquid medicines, troches, gargles and the like. Examples of the quasi-drugs include, but not limited to, toothpaste, mouthwash, halitosis preventive and the like. Examples of the fodder include, but not limited to, various pet foods such as cat food and dog food, baits for ornamental fish and bred fish.

Preferably, the anti-fading agent may be used for beverage and food products. The beverage and food products are not limited insofar as they are rendered colors, and examples of which includes frozen dessert such as ice-creams, ice milk, lacto-ices, sherbets and water ice; beverages such as milk drinks, lactic acid bacteria-containing drinks, fruit drinks, carbonated drinks, fruit juice drinks and powdered drinks; desserts such as puddings (custard pudding, milk pudding, fruit juice pudding and the like); jelly, bavaroise and yogurt; gums (ordinary tabular type; sugar-coated tablet type) such as chewing gum and bubble gum; chocolates such as coating chocolate including marble chocolate, and flavored chocolates including strawberry chocolate, blueberry chocolate, melon chocolate and the like; caramels such as hard candy (including bonbon, butter ball, marble, etc.), soft candy (including caramel, nougat, gummy candy, marshmallow, etc.), drop and toffee; pastries such as hard biscuit, cookies, okaki and senbei; pickles such as asazuke, shoyu-zuke, shio-zuke, miso-zuke, kasu-zuke, kouji-zuke, nuka-zuke, su-zuke, karashi-zuke, moromi-zuke, ume-zuke, fukujin-zuke, siba-zuke, shouga-zuke, chosen-zuke and umezu-zuke; sauces such as separate dressing, non-oil dressing, ketchup, dip and Worcester sauce; jams such as strawberry jam, blueberry jam, marmalade, apple jam, apricot jam and preserve; fruit wines such as red wine; processing fruits such as cherries, apricots, apples and strawberries in syrup; processed meat such as hams, sausages and roasted pork; surimi-based marine products such as fish hams, fish sausages, fish meat paste, kamaboko, chikuwa, hampen, satsuma-age, datemaki and whale bacon; pastas and noodles such as udon, hiyamugi, somen, soba, Chinese noodle, spaghetti, macaroni, rice noodle, starch noodle and wang-tang; and other processed foods including subsidiary food articles of diet, kamaboko, fu and dembu.

As used herein, the wording "colored beverage and food products" means not only the beverage and food products which are colored artificially by adding pigments thereto, but also the beverage and food products whose colors are derived from colors of ingredients contained therein, such as a fruit juice.

The beverage and food products of the present invention can be produced by the conventional manufacturing processes except for adding the anti-fading agent of the invention to a beverage or food product at an arbitrary step in the manufacturing process. Order of the step of adding the anti-fading agent in the manufacturing process are not limited, but it is preferred to carry out the step of adding the anti-fading agent, followed by a step of mixing a pigment, preferably a pigment and flavors, in the presence of the anti-fading agent and then various treatments such as a heating treatment.

For example, in the case of preparing the frozen dessert, an end product may be manufactured by following the steps of adding the anti-fading agent of the invention, acids, emulsifier and stabilizer to a main ingredient of milk, cream, condensed milk, milk powder, sugars, fruits or bean paste; adding flavors to prepare a mixed liquid for frozen dessert; adding and mixing a pigment to the mixed liquid for frozen dessert; filling a container with the mixed liquid after sterilizing and cooling; and cooling or freezing the mixture in the container. In the case of manufacturing beverages, an end product may be produced by following the steps of adding the anti-fading agent of the invention, stabilizer and the like to a main ingredient of sugars, fruit juice or acids; adding flavors and a pigment to the mixture when so required; stabilizing and cooling the mixture; and charging containers with the mixture. When preparing gum products, an end product may be prepared by following the steps of adding sugar, glucose, the anti-fading agent of the invention, citric acid and the like to a gum base which has been heated to gain softness; adding flavors and pigment to the gum base and kneading the gum base mixture; drawing out the gum base mixture by means of a roller to have a certain thickness; cooling the rolled gum base mixture to room temperature; and cutting the rolled gum base mixture to pieces. When manufacturing jellies, an end product may be produced by following the steps of mixing main ingredients of sugar, starch syrup, the anti-fading agent of the invention, citric acid and gelling agent (pectin, agar, gelatin, carrageenan, etc.) in proper ratios; adding flavors and pigment to the mixture; heating and dissolving the mixture; charging containers with the mixture; and cooling the mixture. When preparing the candies, an end product may be prepared by following the steps of adding water to main ingredients of sugar, starch syrup and the like; heating and dissolving the main ingredients; allowing the mixture to stand to be cooled; adding the anti-fading agent of the invention to the mixture; adding flavors and a pigment to the mixture; molding the mixture; and cooling the molded mixture to room temperature. When manufacturing pickles, an end product may be prepared by following the steps of adding sub-ingredients including various seasonings such as salts and sugars, preservatives and the anti-fading agent of the invention to a main ingredient such as vegetables, sea weeds, mushrooms or fruits; adding flavors and a pigment when so required to prepare a pickled product; packing the pickled product into containers; and sterilizing and then cooling the pickled product. When manufacturing dips or dressings, an end product may be prepared by following the steps of adding the anti-fading agent of the invention and a stabilizer or emulsifier to main ingredients of a vegetable oil, soy sauce, sugars, fruit juice, vinegar and salts; adding and mixing flavors and, when so required, a pigment to the dressing liquid; and charging containers with the liquid after sterilizing and cooling.

Amount of the anti-fading agent of the invention to be added to various types of objects such as beverage and food products, cosmetics, pharmaceuticals, quasi-drugs or fodder are not limited insofar as the amounts are effective for preventing the pigments contained in the objects from fading in colors. The amounts can be selected and decided in view of a sugar concentration in an oligosaccharide contained in the anti-fading agent as an active ingredient, type of pigments contained in the objects and an amount thereof and type of the object and ingredients contained therein.

With respect to the various objects such as beverage and food products each containing a pigment in such an amount that an absorbance of the pigments (absorbance of the pigment at a maximum absorption wavelength) are in the range of 0.05–1, content of the anti-fading agent may be at least 0.1 wt. % calculated as an oligosaccharide content. In other words, it is preferable that the anti-fading agent of the invention may be added to the object in such an amount that the oligosaccharide content will be at least 0.1 wt. % with respect to the amount of a pigment which has been added to the object to attain the absorbance (absorbance of the pigment at a maximum absorption wavelength) of 0.05–1.

As described in the following examples, anti-fading effect is improved depending on the oligosaccharide content. Therefore, in terms of the effect of the invention, it is unnecessary to set the upper limit of the content of the anti-fading agent of the invention in an object such as a beverage and food product. Thus, it is possible to decide the content of the anti-fading agent (upper limit) from the view points of taste and physical properties such as viscosity. For example, nigerooligosaccharide, maltooligosaccharide and panose, which are used in the present invention, each has a sweetness of 30–40% of sugar and, therefore, they can exert the anti-fading effect without affecting the taste (sweetness) of the object as being added in the range of 0.1–10 wt. %. In turn, various oligosaccharides per se can be used as sweetening ingredients and, therefore, it is unnecessary to limit the upper limit of the oligosaccharide content.

EXAMPLES

Following experiments, examples and comparative examples will illustrate the present invention in further detail, but the invention is not limited thereto. In addition, "%" appears in the following prescriptions means "wt. %" unless otherwise stated.

Experiment 1

Ingredients of the following prescription are mixed and dissolved so that the nigerooligosaccharide is contained in the mixtures in the form of a nigerooligosaccharide-containing syrup in percentages of 0.5%, 1%, 3%, 5% and 10%. Each of the mixtures was adjusted to have a pH of 3 by using trisodium citrate, and then cooled after heating to a temperature of 93° C., to thereby prepare colored syrups. Pigments used were red cabbage pigment (anthocyanin-based pigment) (0.08 g), Carthamus Yellow pigment (flavonoid-based pigment) (0.03 g), Gardenia Blue (0.08 g), purple sweet potato pigment (flavonoid-based pigment) (0.06 g) and purple corn pigment (flavonoid-based pigment) (0.08 g).

| <Prescription> | |
|---|---|
| High fructose corn syrup (Brix 75°) | 13.3 g |
| Citric acid (crystal) | 0.2 g |
| Nigerooligosaccharide-containing syrup | 0.5–10 g |
| Pigment | 0.03–0.08 g |
| Trisodium Citrate | adjustment (pH3) |
| Water | balance |
| Total | 100 g |

In addition, "nigerooligosaccharide-containing syrup" means a syrup containing nigerooligosaccharide in a solid content of 40% or more (a solid content of 72% or more; same in the following experiments and examples). Further, the absorbance of the colored syrups of above prescriptions based on the pigments contained therein (absorbance of the pigments at a maximum absorption wavelength) were in the range of 0.05–1.

Control syrups in respect of each of the pigments were prepared by mixing above prescriptions other than the nigerooligosaccharide-containing syrup and adding water in place of the nigerooligosaccharide-containing syrup.

Fading in colors of the pigments caused by light (light resistance) were observed by subjecting the samples and controls irradiation with light for 1.5–6 hours at room temperature (20° C.) using a fade meter (600W/m$^2$ (300–700 nm): xenon long-life fade meter XWL75R: product of Suga Test Instruments Co., Ltd.). The light resistant effects of the anti-fading agent of the present invention on the red cabbage pigment, Carthamus Yellow pigment, Gardenia Blue pigment, purple sweet potato pigment and purple corn pigment are shown in FIGS. 1, 2, 3, 4 and 5, respectively. The light resistance were evaluated by measuring the absorbance of the colored syrups of above prescriptions at a maximum absorption wavelength based on the pigment therein before and after the test (light irradiation) and calculating the color persistency (%) from the absorbance after the test (after the light irradiation) with assuming the absorbance before the test (before the light irradiation) as 100%.

As shown in FIGS. 1–5, the anti-fading agent of the invention (nigerooligosaccharide) exhibits a remarkably excellent anti-fading effect (light resistance) with respect to the above pigments depending on the content thereof in the composition, especially with respect to the red cabbage pigment, purple corn pigment and purple sweet potato pigment which are anthocyanin-based pigments, the Carthamus Yellow pigment which is a flavonoid-based pigment and Gardenia Blue pigment.

Experiment 2

Ingredients of the following prescription are dissolved so that nigerooligosaccharide is contained in the mixtures in the form of a nigerooligosaccharide-containing syrup in percentages of 0.5%, 1%, 3%, 5% and 10%, and then the mixtures were heated and cooled to prepare colored syrups.

| <Prescription> | |
|---|---|
| High fructose corn syrup (Brix 75°) | 13.3 g |
| Nigerooligosaccharide-containing syrup | 0.5–10 g |
| Monascus Pigment (azaphilone-based pigment) | 0.08 g |
| Water | balance |
| Total | 100 g |

Absorbance of the colored syrups of above prescriptions based on the pigments contained therein (absorbance of the pigments at a maximum absorption wavelength) were in the range of 0.05–1.

Control syrups in respect of each of the pigments were prepared by mixing above prescriptions other than the nigerooligosaccharide-containing syrup and adding water in place of the nigerooligosaccharide-containing syrup. The compositions were evaluated with respect to the fading in colors by light (light resistance) of the pigments in the same manner as that of Experiment 1. Light resistant effects (anti-fading effects against light) of the anti-fading agent of the invention with respect to the Monascus pigment are shown in FIG. 6.

Figure 6:
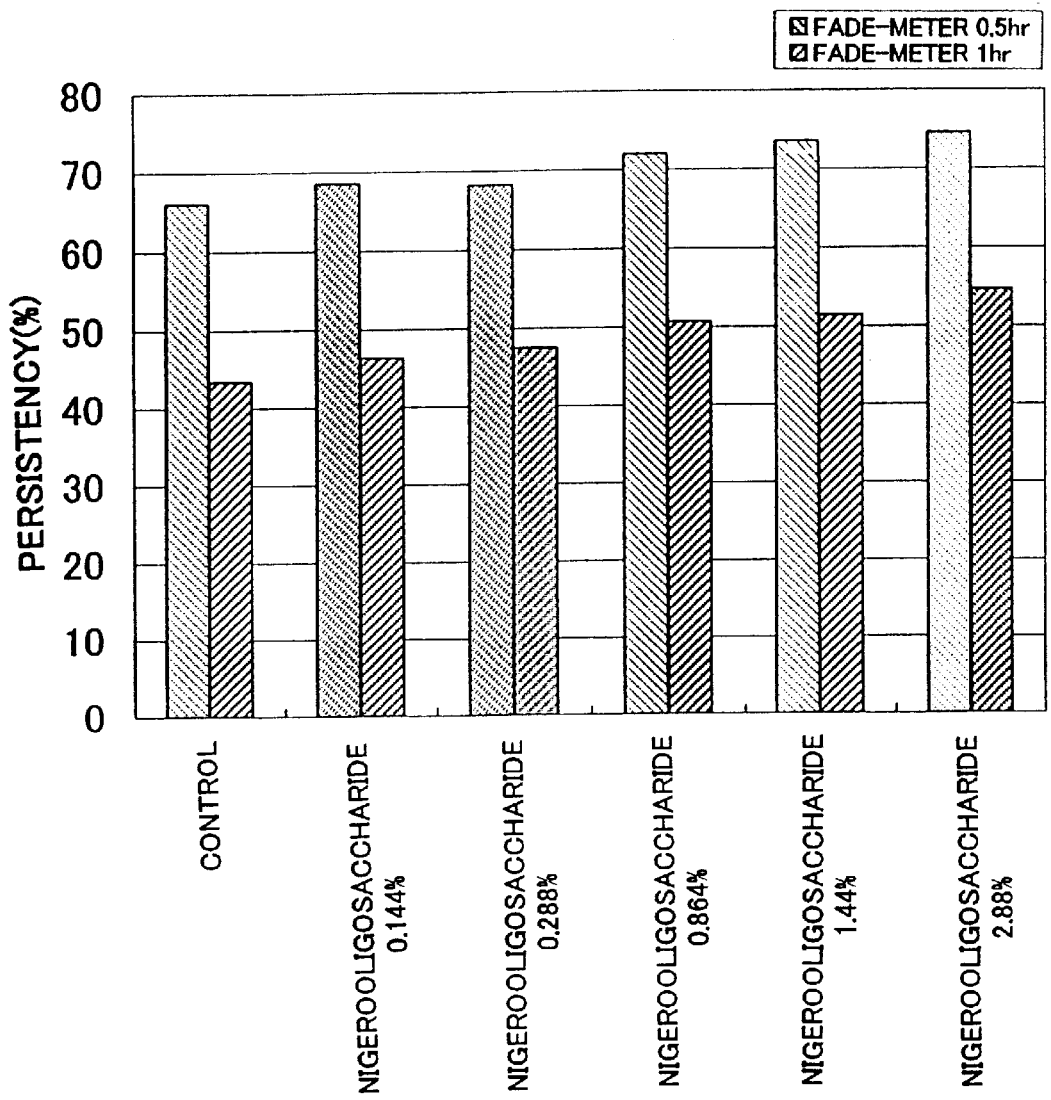
FIG. 6 shows a light-resistance effect (anti-fading effect) of the anti-fading agent (nigerooligosaccharide) of the present invention on the monascus pigment (Experiment 2).
Figure 7:
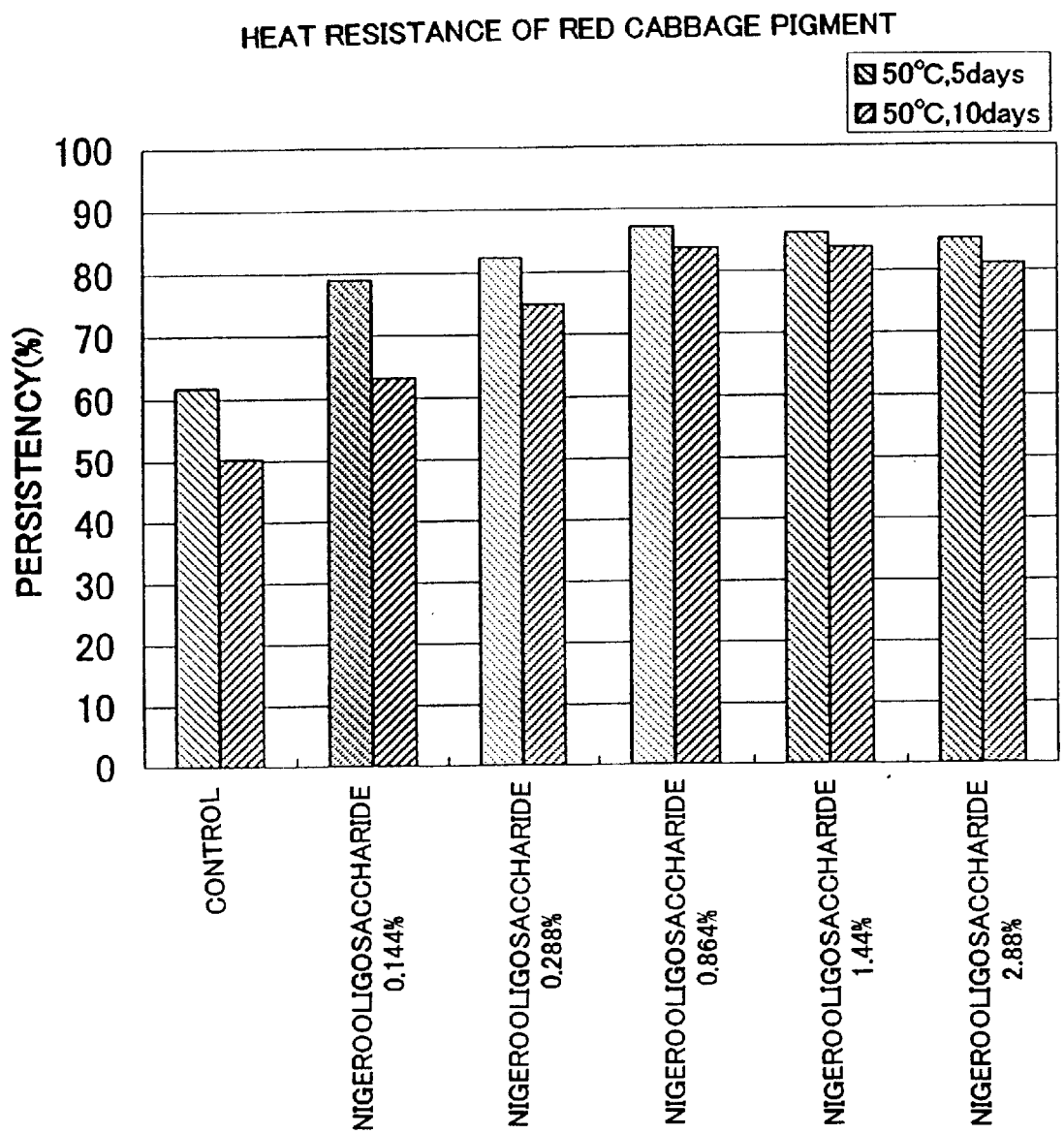
FIG. 7 shows a heat-resistance effect (anti-fading effect) of the anti-fading agent (nigerooligosaccharide) of the present invention on the red cabbage pigment (Experiment 3).
Figure 8:
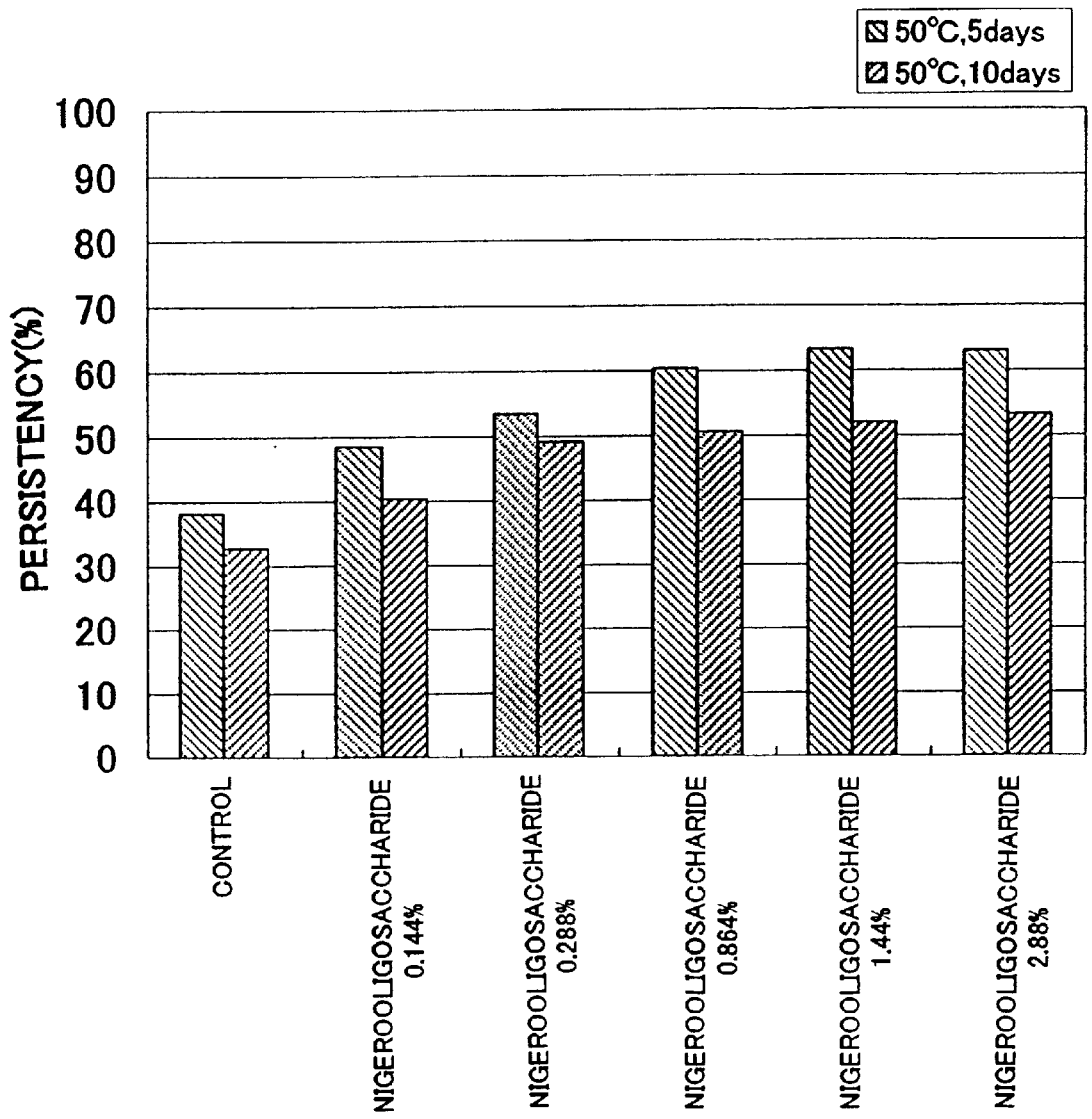
FIG. 8 shows a heat-resistance effect (anti-fading effect) of the anti-fading agent (nigerooligosaccharide) of the present invention on the purple corn pigment (Experiment 3).
Figure 9:
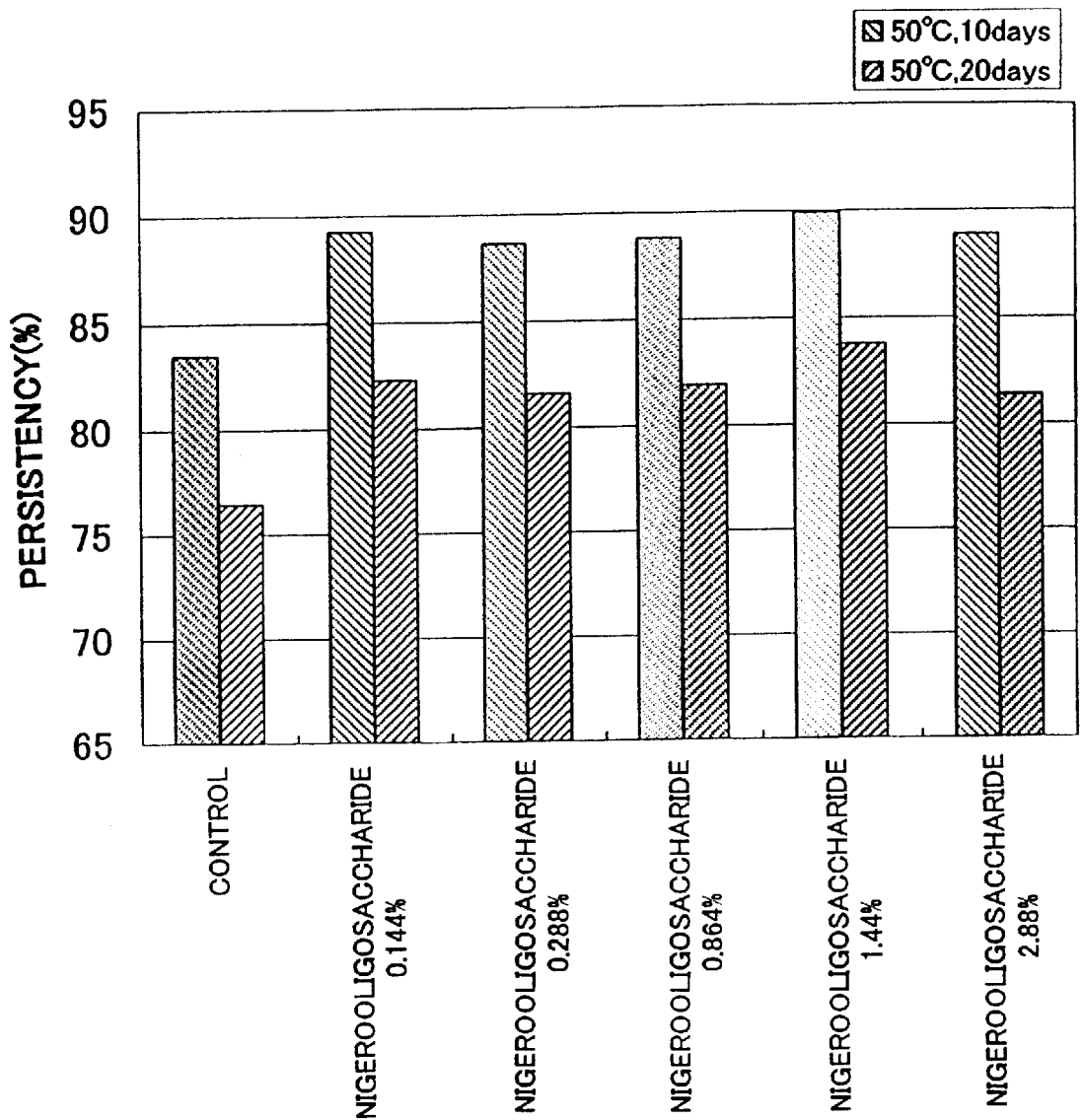
FIG. 9 shows a heat-resistance effect (anti-fading effect) of the anti-fading agent (nigerooligosaccharide) of the present invention on the Gardenia Blue pigment (Experiment 3).
Figure 10:
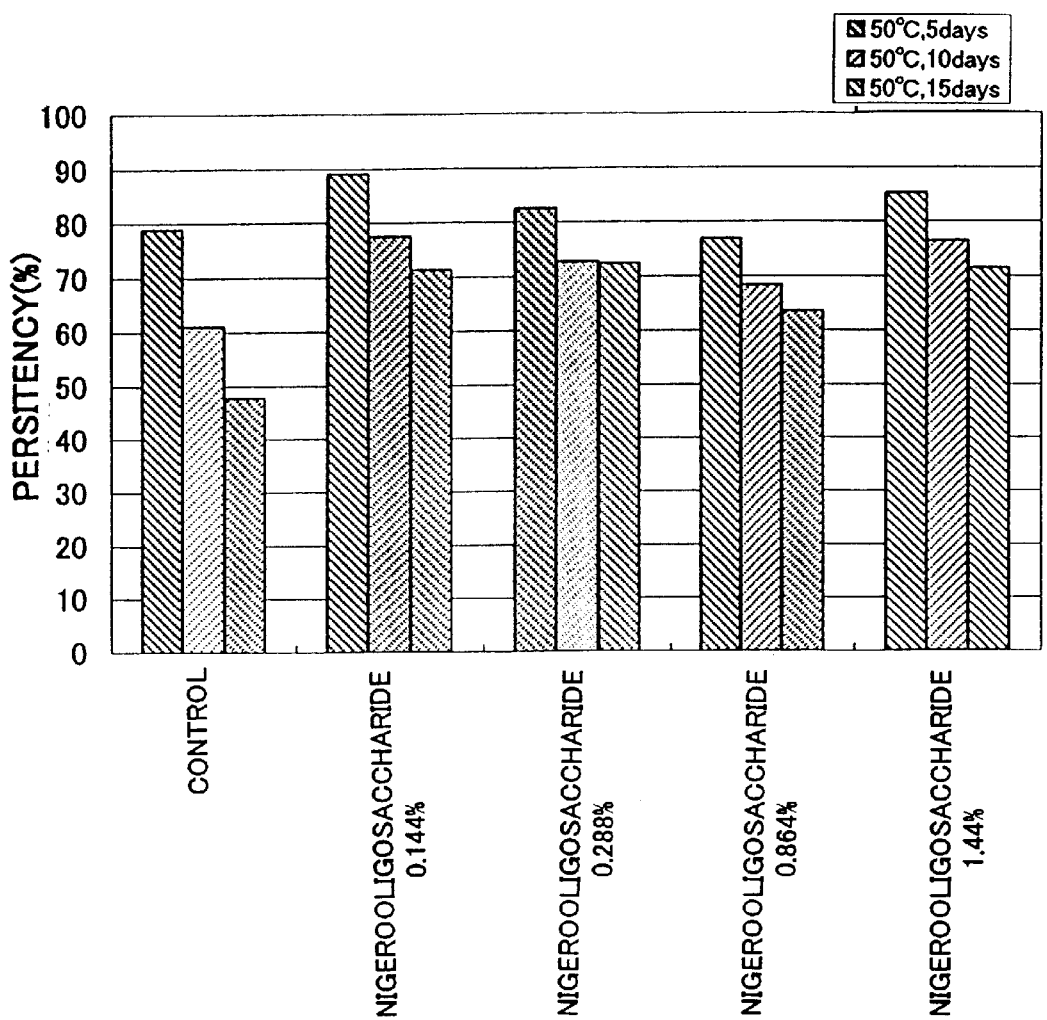
FIG. 10 shows a heat-resistance effect (anti-fading effect) of the anti-fading agent (nigerooligosaccharide) of the present invention on the purple sweet potato pigment (Experiment 3).

As is apparent from FIG. 6, the anti-fading agent of the invention (nigerooligosaccharide) exhibits the anti-fading effect (light resistance) advantageously with respect to the Monascus pigment depending on the content thereof.

Experiment 3

Ingredients of the following prescriptions are dissolved so that nigerooligosaccharide are contained in resultant mixtures in the form of a nigerooligosaccharide-containing syrup in percentages of 0.5%, 1%, 3%, 5% and 10%. Each of the mixtures was adjusted to have a pH of 3 by using trisodium citrate, followed by heating to a temperature of 93° C. and cooling, to thereby give colored syrups. Pigments used were red cabbage pigment (0.08 g), purple corn pigment (0.08 g), Gardenia Blue pigment (0.08 g) and purple sweet potato pigment (0.06 g).

| <Prescription> | |
|---|---|
| High fructose corn syrup (Brix 75°) | 13.3 g |
| Citric acid (crystal) | 0.2 g |
| Nigerooligosaccharide-containing syrup | 0.5–10 g |
| Pigment | 0.06–0.08 g |
| Trisodium Citrate | adjustment (pH3) |
| Water | balance |
| Total | 100 g |

Further, the absorbance of the colored syrups of above prescriptions based on the pigments contained therein (absorbance of the pigments at a maximum absorption wavelength) were in the range of 0.05–1.

Control syrups in respect of each pigments were prepared by mixing above prescriptions other than the nigerooligosaccharide-containing syrup and adding water in place of the nigerooligosaccharide-containing syrup.

The colored syrups and control syrups were incubated in a incubator at a temperature of 50° C., and fading in colors of the pigments were observed at 5–20 days after the start of incubation to evaluate the heat resistance (anti-fading effect against heat). The evaluation of the heat resistance was carried out by measuring each of the absorbance of the colored syrups at a maximum absorption wavelength based on the pigments therein before and after the test (incubation) and calculating a color persistency (%) from the absorbance after the test (incubation) with assuming the absorbance before the test as 100%. The heat resistant effect of the anti-fading agent of the invention with respect to the red cabbage pigment, purple corn pigment, Gardenia Blue pigment and purple sweet potato pigment are shown in FIGS. 7, 8, 9 and 10, respectively.

As is apparent from the FIGS. 7–10, the anti-fading agent of the invention (nigerooligosaccharide) exhibits a remarkable anti-fading effect with respect to above pigments, especially with respect to the red cabbage pigment, purple corn pigment and Gardenia Blue pigment substantially depending on the content thereof. Besides, Experiment 3 reveals that the purple sweet potato pigment has a significant anti-fading effect (heat resistance) which becomes more prominent as the incubation time is increased. It was thus revealed that the fading in colors of the purple sweet potato pigment caused by the long-term incubation at high temperature is excellently suppressed by the anti-fading agent of the present invention.

Experiment 4

Anti-fading effect against light and heat of various types of sugars (subject sugars) are investigated with respect of red cabbage pigment, purple sweet potato pigment and Carthamus Yellow pigment. More specifically, the ingredients of the following prescriptions are dissolved so that the red cabbage pigment, purple sweet potato pigment or Carthamus Yellow pigment are respectively contained in the mixtures in percentages of 0.08%, 0.06% or 0.03%. Each of the mixtures were adjusted to have a pH of 3 by using trisodium citrate, followed by heating to a temperature of 93° C. and cooling, to thereby give colored syrups. The subject sugars used were high fructose corn syrup, nigerooligosaccharide, maltooligosaccharide, isomaltooligosaccharide, panose, glucosylsucrose, fructooligosaccharide, soybean oligosaccharide, galactooligosaccharide, gentiooligosaccharide, xylooligosaccharide and lactooligosaccharide, a nd each of which is used in an amount of 3% with respect to the purple sweet potato pigment and 10% with respect to the red cabbage pigment and Carthamus Yellow pigment. Further, panose was used in the form of a panose syrup having a solid panose content of 75%.

| <Prescription> | |
| --- | --- |
| High fructose corn syrup (Brix 75°) | 13.3 g |
| Citric acid (crystal) | 0.2 g |
| Subject Sugar | 3 g |
| | or |
| | 10 g |
| Pigment | 0.03–0.08 g |
| Trisodium Citrate | adjustment (pH3) |
| Water | balance |
| Total | 100 g |

Further, the absorbance of the colored syrups of above prescriptions based on the pigments contained therein (absorbance of the pigments at a maximum absorpti on wavelength) were in the range of 0.05–1.

Control syrups in respect of each of the pigments were prepared by mixing above prescriptions other than the subject sugars and adding water in place of the subject sugars.

Light resistance of the colored syrups and control syrups were evaluated in the same manner as in Experiment 1, specifically by observing the degree of fading in colors by light after 2.5–3 hours of irradiation by means of the xenon fade meter (600W/m$^2$) at a room temperature of 20° C. Heat resistance of the colored syrups and control syrups were evaluated in the same manner as in Experiment 3, specifically by observing the degree of fading in colors of pigments by heat after incubating them at a temperature of 50° C. for 15–40 days.

Figure 13:
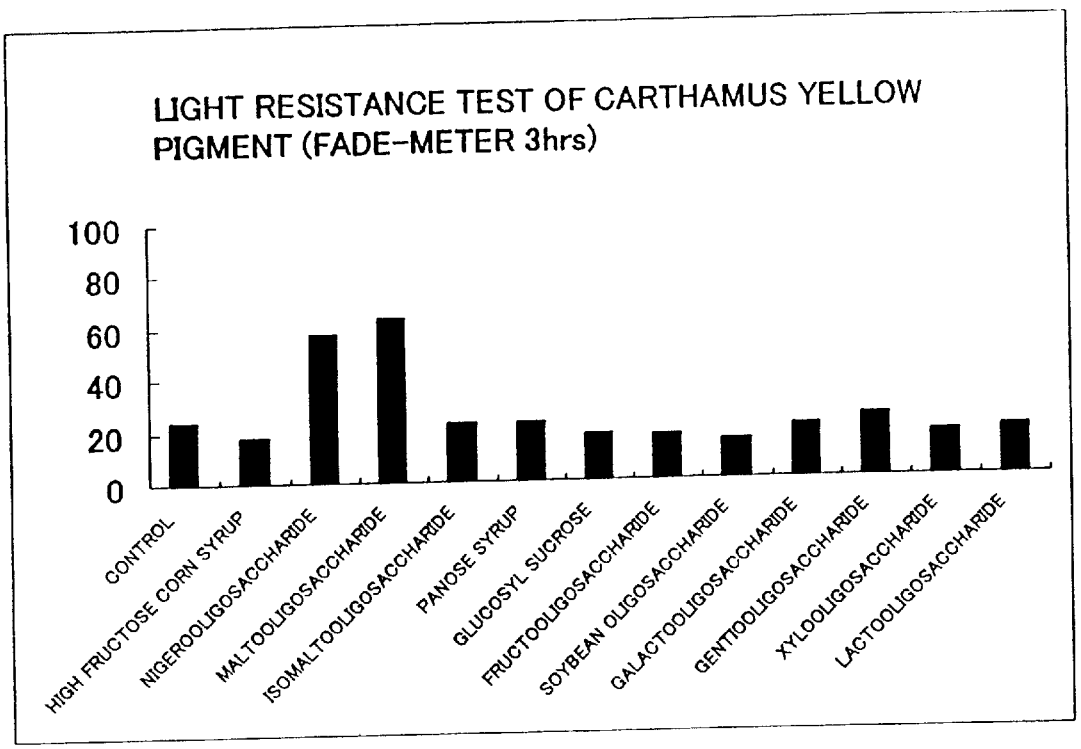
FIG. 13 shows anti-fading effects of the subject sugars on the Carthamus Yellow pigment (light-resistance) (Experiment 4).
Figure 19:
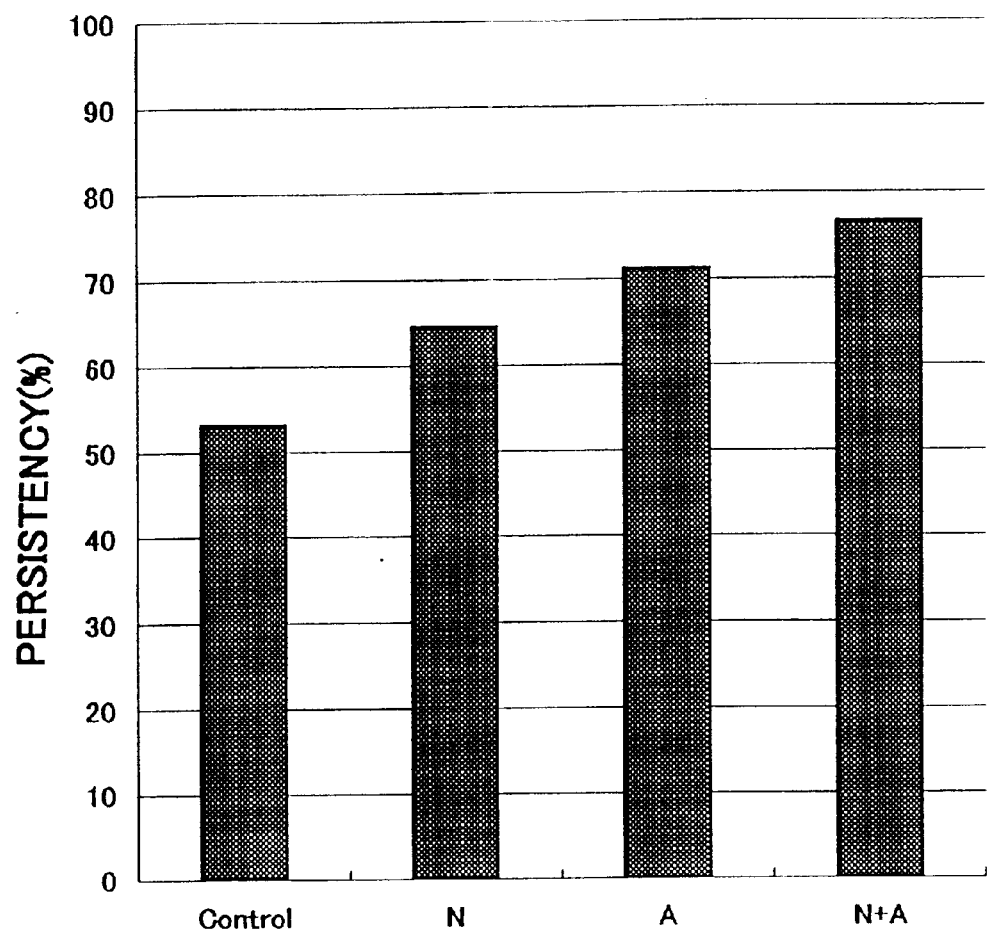
FIG. 19 shows anti-fading effects of nigerooligosaccharide and of nigerooligosaccharide and antioxidant (light resistance against irradiation with ultraviolet rays) on the Gardenia Blue pigment (Experiment 5).
Figure 20:
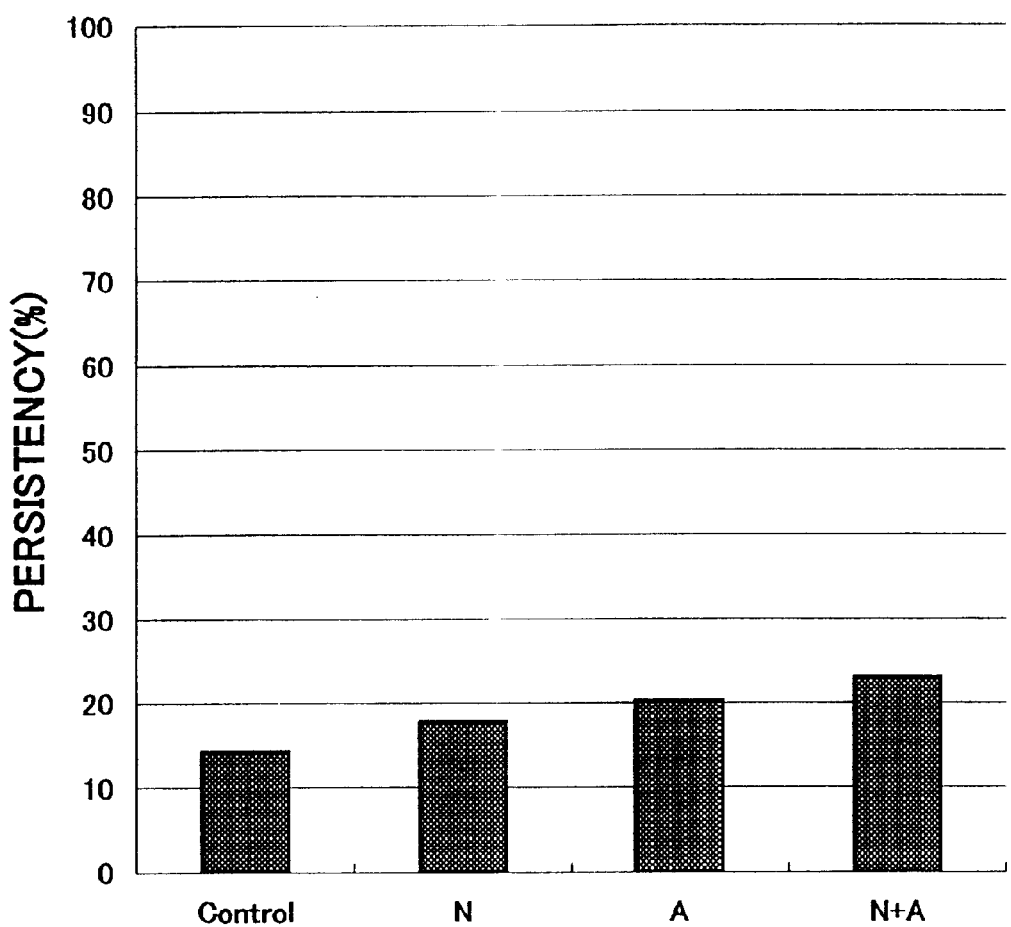
FIG. 20 shows anti-fading effects of nigerooligosaccharide and of nigerooligosaccharide and antioxidant (light resistance against irradiation with ultraviolet rays) on the Carthamus Yellow pigment (Experiment 5).

The anti-fading effects of the subject sugars with respect to the red cabbage pigment, purple sweet potato pigment and Carthamus Yellow pigment are shown in FIGS. 11, 12 and 13, respectively. In addition, A in FIGS. 11 and 12 each shows the anti-fading effect against light (light resistance) and B in FIGS. 11 and 12 each shows the anti-fading effect against heat (heat resistance) of the subject sugars.

As is apparent from FIGS. 11–13, the nigerooligosaccharide, maltooligosaccharide and panose are capable of suppressing the fading in colors by light of the anthocyanin-based pigments such as red cabbage pigment and purple sweet potato pigment and flavonoid-based pigments such as Carthamus yellow pigment as well as of suppressing the fading in colors by heat of the anthocyanin-based pigments and, further, these sugars, especially the nigerooligosaccharide and the maltooligosaccharide are significantly excellent in the anti-fading effects compared to other sugars.

Experiment 5

Ingredients of the following prescriptions are mixed and dissolved, and each of the mixtures was adjusted by using trisodium citrate to have a pH of 3. The mixtures were then heated to a temperature of 90° C. and cooled to give colored acid syrups (prepared were nigerooligosaccharide-containing liquid which contains no antioxidant, antioxidant-containing liquid which contains no nigerooligosaccharide and nigerooligosaccharide and antioxidant-containing liquid). Pigments used were purple corn pigment, red cabbage pigment, purple sweet potato pigment, Gardenia Red pigment, cochineal pigment (quinoid-based pigment), Gardenia Blue pigment and Carthamus Yellow pigment.

| <Prescription> | |
| --- | --- |
| High fructose corn syrup (Brix 75°) | 10 g |
| Nigerooligosaccharide-containing syrup | 0 |
| | or |
| | 1 g |
| Antioxidant | 0 |
| | or |
| | 0.05 g |
| Pigment | 0.04 g |
| Citric acid | 0.2 g |
| Trisodium Citrate | adjustment (pH3) |
| Water | balance |
| Total | 100 g |

Used for the antioxidant was an enzymatically modified isoquercitrin {SANMELIN AO-1007 (a formulation containing 15% enzymatically modified isoquercitrin); product of San-Ei Gen F.F.I., INC.}. Further, absorbance of the colored acid syrups of above prescriptions based on the pigments contained therein (absorbance of the pigments at a maximum absorption wavelength) were in the range of 0.05–1.

Control syrups in respect of each of the pigments were prepared by mixing above prescriptions other than the nigerooligosaccharide-containing syrup and oxidant, and adding water in place of them.

Fading caused by ultraviolet rays of the pigments contained in the colored acid syrups and the control syrups were observed in the same manner as in Experiment 1 by irradiating the subjects with ultraviolet rays for 4–8 hours at a temperature of 20° C. by using a carbon arc fade meter (500W/m$^2$: ultraviolet rays long-life fade meter FIAL-3: Suga Test Instruments CO., Ltd.). Further, fading in colors caused by fluorescent light of the pigments contained in the colored acid syrups and the control syrups were observed by irradiating the subjects the fluorescent light for 72 hours at a temperature of 10° C. by using an environment controller (product of Nippon Medical & Chemical Instruments Co., Ltd.; 20,0001x). The anti-fading effects (light resistance) were evaluated by measuring the absorbance of the colored acid syrups at a maximum absorption wavelength based on the pigment contained therein before and after the test (before and after the irradiation with ultraviolet rays or fluorescent rays) and calculating the color persistency (%) from the absorbance after the test (after the irradiation with ultraviolet rays or fluorescent light) assuming the absorbance before the test (before the irradiation with ultraviolet rays or fluorescent light) as 100%. FIGS. 14, 15, 16, 17, 18, 19 and 20 respectively show the anti-fading effects of nigerooligosaccharide and of nigerooligosaccharide used in combination with an antioxidant with respect to the purple corn pigment, red cabbage pigment, purple sweet potato pigment, Gardenia Red pigment, cochineal pigment, Gardenia Blue pigment and Carthamus Yellow pigment. A in FIGS. 14–18 each shows the light resistance with respect to ultraviolet rays, and B in FIGS. 14–18 each shows the light resistance with respect to fluorescent light.

It is apparent from these drawings that nigerooligosaccharide is capable of advantageously suppressing not only the fading in colors of the pigments caused by irradiation with ultraviolet rays, but also the fading in colors of the pigment caused by irradiation with fluorescent light, and that use of the antioxidant in combination with the nigerooligosaccharide improves the anti-fading effects of nigerooligosaccharide.

Experiment 6

Figure 21:
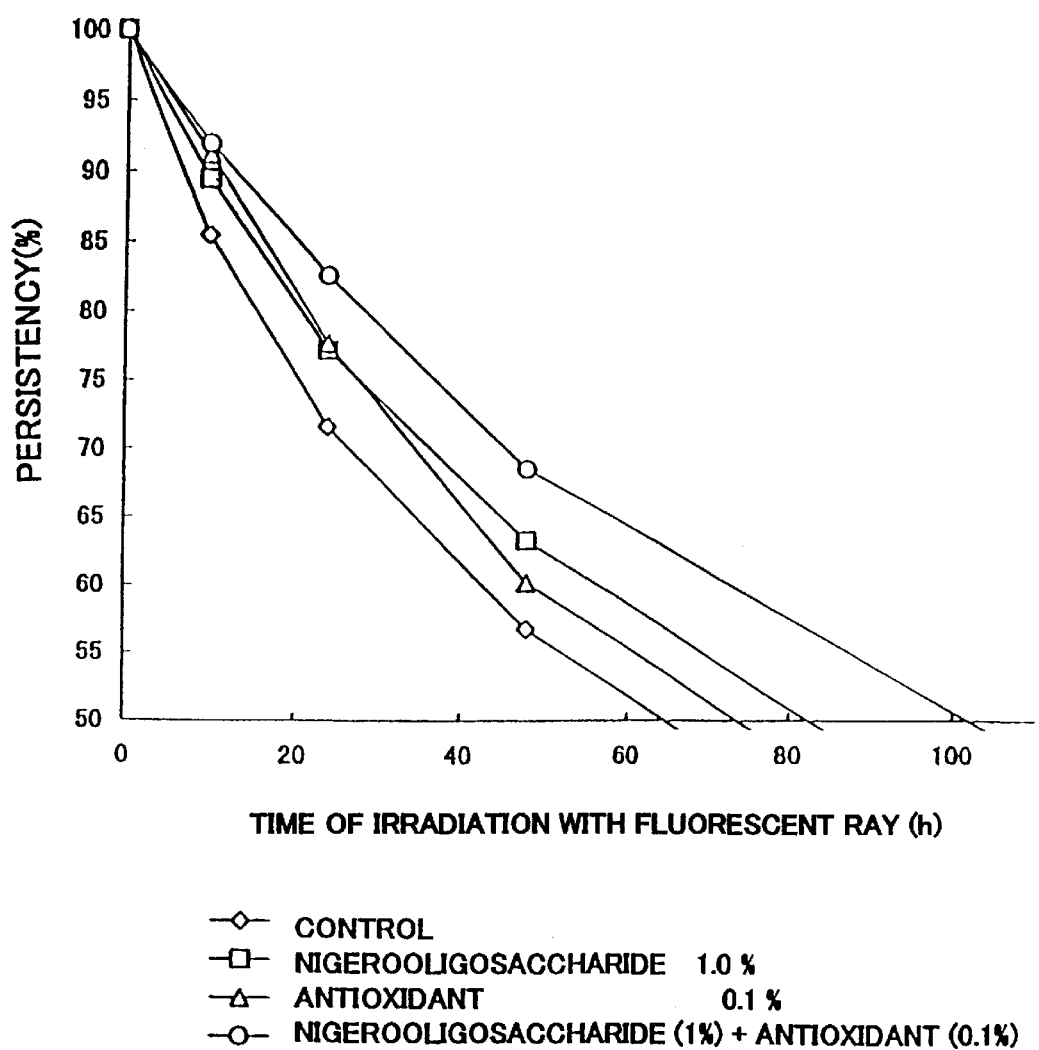
FIG. 21 shows results of Experiment 6, wherein the fading in colors with time of the purple corn pigment caused by irradiation with fluorescent rays in the presence of nigerooligosaccharide, antioxidant, or nigerooligosaccharide and antioxidant is observed.

Prepared were colored acid syrups using the purple corn pigment, whose anti-fading effect was confirmed in Experiment 5, in the same manner as in Experiment 5 (nigerooligosaccharide-containing liquid (which contains no antioxidant), antioxidant-containing liquid (which contains no nigerooligosaccharide) and nigerooligosaccharide and antioxidant-containing liquid). Fading in color of the pigment with time caused by fluorescent light was observed by irradiating the fluorescent light for a long time using an environment controller at a temperature of 10° C. Further, a control syrup which contains neither nigerooligosaccharide nor antioxidant was also prepared, and fading in color of the pigment thereof was observed in the same manner as described above. Results of the observations are shown in FIG. 21. In FIG. 21, "persistency" means a percentage of absorbency (persistency (%)) of the purple corn pigment at each of the specified time points during the irradiation with fluorescent light with respect to absorbency (100%) of the pigment before the irradiation with fluorescent light.

It is apparent from the figure that the antioxidant is effective against the fading in color caused by the irradiation with fluorescent light for a short period of time, while the nigerooligosaccharide has a significant suppressing effect against fading in color of the pigment caused by the irradiation with fluorescent light for a long period of time, and that the suppressing effect is enhanced by using the antioxidant and nigerooligosaccharide in combination (anti-fading effect for a short period of time and long period of time).

Example 1

Peach Soda

After mixing ingredients of the following prescription and filtering the mixture, the mixture was poured into a bottle and sterilized at a temperature of 90° C. for 30 minutes, to thereby give a peach soda beverage. The asterisk in the prescription indicates that the ingredient is a product of San-Ei Gen F.F.I., INC. (same applies to the following Examples).

| <Prescription> | |
| --- | --- |
| Water | 100 ml |
| High fructose corn syrup (Brix 75°) | 10 ml |
| Nigerooligosaccharide-containing syrup | 20 ml |
| Peach flavour | 0.3 ml |
| Purple sweet potato pigment (SAN RED YMF)* | 0.02 ml |
| Citric acid | adjustment (pH 3.3) |
| Carbonated water | balance |
| Total | 200 ml |

A control peach soda (Comparative Example 1) was prepared by adding 10 ml of the high fructose corn syrup in place of the nigerooligosaccharide-containing syrup (total amount of the high fructose corn syrup in this control peach soda is 20 ml). Both of the peach soda were subjected to irradiation with fluorescent light of 3000 lx for 3 days in a cooled place (at a temperature of 5–10° C.), to observe fading in color of the pigment caused by light (light resistance). Further, both of the peach soda were subjected to a heat treatment at a temperature of 95° C. for 40 minutes to observe fading in color of the pigment caused by heat (heat resistance). Results are shown in Table 1. Evaluation of the light resistance and heat resistance were carried out by macroscopic test and indicated as color persistency after the light irradiation and the heat treatment with setting the degree of coloring before the light irradiation and heat treatment as 100%.

TABLE 1

| | Light Resistance (%) | Heat Resistance (%) | Color Tone |
| --- | --- | --- | --- |
| Example 1 | 80–90 | 70–80 | bright red |
| Comparative Example 1 | 50–60 | 40–50 | purple |

As is apparent from the results, the peach soda prepared by using the anti-fading agent of the present invention scarcely changes in the color tone (scarcely fades in color) by light or heat and are excellent in light resistance and heat resistance in comparison to that prepared by using the high fructose corn syrup only.

Example 2

Strawberry Jelly

After mixing ingredients of the following prescription and heating at a temperature of 80° C. to dissolve them, the mixture was poured into a cup and cooled at a temperature of 5° C. for 1 hour, to thereby give a strawberry jelly.

| <Prescription> | |
| --- | --- |
| Water | 28 g |
| Pectin | 1.3 g |
| Sugar | 50 g |
| Nigerooligosaccharide-containing syrup | 5 g |
| Citric acid | 0.4 g |
| Starch syrup | 50 g |
| Red cabbage pigment (SAN RED RCA)* | 0.1 ml |
| Sodium citrate | adjustment (pR 4.2) |
| Strawberry flavoring | optimum |

A control strawberry jelly (Comparative Example 2) was prepared by adding water in place of the nigerooligosaccharide-containing syrup. The strawberry jellies of Example 2 and Comparative Example 2 were subjected to irradiation with fluorescent light of 3000 lx for 3 days to observe by naked eye the fading caused by light in color of the jelly (light resistance). Further, the strawberry jellies were kept in a incubator at a temperature of 35° C. for 7 days to observe by naked eye the fading caused by heat in color of the jelly (heat resistance). Results are shown in Table 2. Evaluation of the light resistance and heat resistance were carried out based on color persistency after the light irradiation and the heat treatment with setting the degree of coloring before the light irradiation and heat treatment as 100%.

TABLE 2

|  | Light Resistance (%) | Heat Resistance (%) | Color Tone |
| --- | --- | --- | --- |
| Example 2 | 80–90 | Not less than 90 | bright red |
| Comparative Example 2 | 70–80 | 50–60 | purple red |

As is apparent from the results, the strawberry jelly prepared by using the anti-fading agent of the invention scarcely changes in the color tone (scarcely fades in color) by light or heat and is excellent in light resistance and heat resistance.

Example 3

Non-oil Dressing (Apricot and Perrila Dressing)

Ingredients of the following prescription are mixed and filtered, and then the mixture was poured into a bottle. The mixture in the bottle was sterilized at a temperature of 90° C. for 30 minutes, to thereby give a non-oil dressing.

| <Prescription> | |
| --- | --- |
| Vinegar (acidity: 4.2%) | 14.0 kg |
| Apple vinegar (acidity: 5%) | 6.0 kg |
| Maltooligosaccharide | 10.0 kg |
| Salted and fermented seafood | 5.0 kg |
| Sake | 5.0 kg |
| Transparent lemon juice | 7.0 kg |
| Monosodium L-glutamate | 1.0 kg |
| Salted Japanese apricot | 5.0 kg |
| Sugar | 2.0 kg |
| Salt | 2.0 kg |
| Dried perrila flake | 0.1 kg |
| Powdered black pepper | 0.05 kg |
| Skipjack-flavored seasoning (SAN LIKE powdered skipjack-U)* | 0.6 kg |
| Beef-flavored seasoning (SAN LIKE beef extract)* | 0.3 kg |
| Perrila flavor | 0.2 kg |
| Red cabbage pigment (SAN RED RCA)* | 0.1 kg |
| Pure water | balance |
| Total | 100.0 kg |

Example 4

Fruit Drink

Ingredients of the following prescription are mixed and filtered, and then the mixture was poured into a bottle. The mixture in the bottle was sterilized at a temperature of 90° C. for 30 minutes, to give a fruit drink.

| <Prescription> | |
| --- | --- |
| Sugar | 7.5 kg |
| High fructose corn syrup | 5.0 kg |
| Panose syrup | 3.0 kq |
| Nigerooligosaccharide syrup | 3.0 kg |
| Concentrated white grape juice (quintuple strength) | 2.2 kg |
| Citric acid (crystals) | 0.225 kg |
| Grape flavoring* | 0.1 kg |
| Antioxidant (SANMELIN A0-1007)* | 0.1 kg |
| L-ascorbic acid | 0.025 kg |
| Red cabbage pigment (SAN RED RCF)* | 0.1 kg |
| Pure water | balance |
| Total amount | 100.0 kg |

Example 5

Syrup (Lemon-flavored) for Chipped Ice

Ingredients of the following prescription are mixed and filtered, and the mixture was poured into a bottle. The mixture in the bottle was sterilized at a temperature of 90° C. for 30 minutes, to give a syrup for chipped ice.

| <Prescription> | |
| --- | --- |
| High fructose corn syrup | 65.0 kg |
| Panose syrup | 5.0 kg |
| Citric acid (crystal) | 0.25 kg |
| Trisodium citrate | 0.05 kg |
| Antioxidant (SANMELIN A0-1007)* | 0.05 kg |
| Lemon extract* | 0.3 kg |
| Carthamus yellow pigment (SAN YELLOW NO.2SF)* | 0.35 kg |
| Pure water | Balance |
| Total | 100.0 kg |

As explained above, oligosaccharides such as nigerooligosaccharide, maltooligosaccharide or panose can impart a resistance against light (sunlight, fluorescent light, etc.) and heat to synthetic and natural pigments, especially to the natural pigments, and advantageously inhibit fading or change in colors of the pigments caused by light or heat. Further, nigerooligosaccharide, maltooligosaccharide and panose used in the present invention are safe as is apparent that they have heretofore been used for the preparation of food products. They are thus useful as anti-fading agents for various products for which the safety is the most important issue, especially for beverage and food products, cosmetics and pharmaceuticals. These saccharide can impart excellent light resistance and heat resistance to beverage and food products containing anthocyanin-based pigments or flavonoid-based pigments without changing the tastes thereof.

What is claimed is:

1. A method for inhibiting fading in color of a natural pigment, the method comprising adding at least one oligosaccharide selected from the group consisting of nigerooligosaccharide, maltooligosaccharide and panose, or adding an antioxidant and at least one oligosaccharide selected from the group consisting of nigerooligosaccharide, maltooligosaccharide and panose, to the natural pigment.

2. The method for inhibiting fading in color of a natural pigment according to claim 1, wherein the pigment is at least one natural pigment selected from the group consisting of carotenoid-based pigments, quinoid-based pigments, anthocyanin-based pigments, flavonoid-based pigments, azaphilone-based pigments, betacyanin-based pigments, Gardenia Blue pigment and Gardenia Red pigment.

3. The method for inhibiting fading in color of a natural pigment according to claim 1, wherein the fading in color of the pigment occurs due to light irradiation.

4. The method for inhibiting fading in color of a natural pigment according to claim 1, wherein the fading in color of the pigment occurs due to heat treatment.

5. The method for inhibiting fading in color of a natural pigment according to claim 1, wherein the antioxidant is at least one antioxidant selected from the group consisting of a Chinese bayberry extract, rutin extract, coffee bean extract, rosemary extract, enzyratically modified rutin and enzymatically modified isoquercitrin.

6. The method for inhibiting fading in color of a natural pigment according to claim 1, wherein a proportion of the antioxidant is 0.5–100 parts by weight to 100 parts by weight of the oligosacchanide content.

7. The method for inhibiting fading in color of a natural pigment according to claim 1, wherein a proportion of the oligosaccharide is at least 0.1 wt. % to beverages and food products each containing the natural pigment in an amount that an absorbance of the pigment at a maximum absorption wavelength is in the range of 0.05–1.

* * * * *